US011213509B2

(12) United States Patent
Baguisi et al.

(10) Patent No.: US 11,213,509 B2
(45) Date of Patent: *Jan. 4, 2022

(54) COMPOSITIONS AND METHODS FOR TREATING TRAUMATIC BRAIN INJURY

(71) Applicant: Ischemix, LLC, North Grafton, MA (US)

(72) Inventors: Alexander Baguisi, South Grafton, MA (US); Reinier Beeuwkes, Concord, MA (US); Ralph Casale, Westford, MA (US); David A. DeWahl, Jr., Greenwich, CT (US); Steven A. Kates, Needham, MA (US); Alan S. Lader, Stoughton, MA (US)

(73) Assignee: ISCHEMIX, LLC, Grafton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/943,088

(22) Filed: Jul. 30, 2020

(65) Prior Publication Data

US 2020/0352904 A1 Nov. 12, 2020

Related U.S. Application Data

(63) Continuation of application No. 15/962,575, filed on Apr. 25, 2018, now Pat. No. 10,744,115.

(60) Provisional application No. 62/489,735, filed on Apr. 25, 2017.

(51) Int. Cl.
| | | |
|---|---|---|
| *A61K 31/385* | (2006.01) | |
| *A61P 25/28* | (2006.01) | |
| *A61K 31/662* | (2006.01) | |
| *A61K 45/06* | (2006.01) | |
| *A61K 31/661* | (2006.01) | |
| *A61K 31/4178* | (2006.01) | |

(52) U.S. Cl.
CPC ........ *A61K 31/385* (2013.01); *A61K 31/4178* (2013.01); *A61K 31/661* (2013.01); *A61K 31/662* (2013.01); *A61K 45/06* (2013.01); *A61P 25/28* (2018.01)

(58) Field of Classification Search
CPC .... A61K 31/385; A61K 31/662; A61K 45/06; A61K 31/661; A61K 31/4178; A61P 25/28
See application file for complete search history.

(56) References Cited

U.S. PATENT DOCUMENTS

| | | | |
|---|---|---|---|
| 3,875,207 A | 4/1975 | Iselin et al. | |
| 5,318,987 A | 6/1994 | Wieithmann et al. | |
| 5,288,706 A | 12/1994 | Yamanouchi et al. | |
| 5,455,264 A | 10/1995 | Beisswenger et al. | |
| 6,013,663 A | 1/2000 | Fujita et al. | |
| 6,127,339 A | 10/2000 | Hatanaka et al. | |
| 6,271,254 B1 | 8/2001 | Ulrich et al. | |
| 6,348,490 B1 | 2/2002 | Hettch et al. | |
| 6,441,024 B1 | 8/2002 | Klatt et al. | |
| 6,544,718 B2 | 4/2003 | Goto | |
| 6,890,896 B1 | 5/2005 | Shashoua | |
| 7,030,154 B2 | 4/2006 | Ames | |
| 7,202,270 B2 | 4/2007 | Majeed et al. | |
| 7,524,819 B2 | 4/2009 | Shashoua | |
| 7,928,067 B2 | 4/2011 | Baguisi et al. | |
| 8,410,162 B2 | 4/2013 | Garner et al. | |
| 8,772,249 B2 | 7/2014 | Baguisi et al. | |
| 8,772,250 B2 * | 7/2014 | Baguisi ................ | A61K 31/385 514/21.91 |
| 8,815,937 B2 | 8/2014 | Baguisi et al. | |
| 9,359,325 B2 | 6/2016 | Baguisi et al. | |
| 9,540,417 B2 | 1/2017 | Baguisi et al. | |
| 2002/0035243 A1 | 3/2002 | Imfeld et al. | |
| 2002/0048798 A1 | 4/2002 | Avery et al. | |
| 2004/0204340 A1 | 10/2004 | Hamilton et al. | |
| 2005/0153291 A1 | 7/2005 | Harwich et al. | |
| 2006/0019901 A1 | 1/2006 | Shashoua | |
| 2007/0287195 A1 | 12/2007 | Suda | |
| 2009/0082281 A1 | 3/2009 | Shashoua | |

(Continued)

FOREIGN PATENT DOCUMENTS

| | | |
|---|---|---|
| CA | 2582027 | 9/2007 |
| DE | 10 47 991 B | 12/1958 |

(Continued)

OTHER PUBLICATIONS

Greve et al. in Mount Sinai Journal of Medicine76:97-104 (2009) (Year: 2009).*
Adger, B., et al., "The Synthesis of ®-(+)-Lipoic Acid Using a Monooxygenase-Catalysed Biotransformation as the Key Step," Bioorganic and Mechanical Chemistry, 5(2): 253-261 (1997).
Anderson, MD, Cancer Center News Release Dated Feb. 25, 2010, "New Strategy Develops Two Prototype Drugs Against Cancer, Retinal Diseases," Retrieved from internet on Dec. 1, 2010: http://www.mdanderson.org/newsroom/news-releases/2010/new-strategy-develops-two-pr[insert 3 periods], 4 pages.

(Continued)

*Primary Examiner* — Dennis Heyer
(74) *Attorney, Agent, or Firm* — Hamilton, Brook, Smith & Reynolds, P.C.

(57) ABSTRACT

The present invention relates, in certain embodiments, to methods for preventing and/or treating neurodegenerative damage (e.g., secondary cascade of neurodegenerative damage) and improving functional outcomes (e.g., outcomes associated with cognitive, behavior and sensorimotor function) caused by traumatic brain injury using neuroprotective lipoyl compounds. The present invention also provides, in various embodiments, compositions for use in treating and/or preventing TBI in a subject in need thereof, compounds for use in the manufacture of a medicament for treating and/or preventing TBI in a subject in need thereof, and methods of preparing a pharmaceutical composition for treating and/or preventing secondary brain damage caused by TBI.

20 Claims, 15 Drawing Sheets

(56) References Cited

U.S. PATENT DOCUMENTS

| | | |
|---|---|---|
| 2009/0306190 A1 | 12/2009 | Stenzel-Poore et al. |
| 2010/0292313 A1 | 11/2010 | Baguisi et al. |
| 2010/0317873 A1 | 12/2010 | Chiu |
| 2011/0160294 A1 | 6/2011 | Baguisi et al. |
| 2012/0135932 A1 | 5/2012 | Baguisi et al. |
| 2013/0237483 A1 | 9/2013 | Baguisi et al. |
| 2014/0274917 A1 | 9/2014 | Baguisi et al. |
| 2015/0065564 A1 | 3/2015 | Baguisi et al. |
| 2015/0329519 A1 | 11/2015 | Kates et al. |
| 2016/0264622 A1 | 9/2016 | Baguisi et al. |

FOREIGN PATENT DOCUMENTS

| | | |
|---|---|---|
| EP | 0 063 879 | 11/1989 |
| EP | 0 424 282 | 4/1991 |
| EP | 0 869 126 | 7/2002 |
| EP | 1 371 640 | 12/2003 |
| EP | 1 454 627 | 9/2004 |
| JP | 9-90542 | 4/1997 |
| JP | 11-7099 | 1/1999 |
| JP | 2000 169371 | 6/2000 |
| JP | 2003 048833 | 2/2003 |
| JP | 2003-518477 | 6/2003 |
| JP | 2003-286168 | 10/2003 |
| JP | 2004-51624 | 2/2004 |
| JP | 2006-22066 | 1/2006 |
| JP | 2007 070303 | 3/2007 |
| KR | 1998-081044 | 11/1998 |
| WO | WO 1993/022320 | 11/1993 |
| WO | WO 1997/018235 | 5/1997 |
| WO | WO 1999/045922 | 9/1999 |
| WO | WO 2001/009118 | 2/2001 |
| WO | WO 2001/036454 | 5/2001 |
| WO | WO 2001/080851 A1 | 11/2001 |
| WO | WO 2002/096360 | 12/2002 |
| WO | WO 2003/055853 | 7/2003 |
| WO | WO 2003/070714 | 8/2003 |
| WO | WO 2003/072052 | 9/2003 |
| WO | WO 2004/004632 | 1/2004 |
| WO | WO 2005/063732 | 7/2005 |
| WO | WO 2006/101909 | 9/2006 |
| WO | WO 2006/101910 | 9/2006 |
| WO | WO 2006/117995 | 11/2006 |
| WO | WO 2007/027559 A2 | 3/2007 |
| WO | WO 2010/052310 A1 | 5/2010 |
| WO | WO 2010/132657 A1 | 11/2010 |
| WO | WO 2010/147957 | 12/2010 |
| WO | WO 2011/080725 | 7/2011 |
| WO | WO 2012/067947 A1 | 5/2012 |
| WO | WO 2015/174948 A1 | 11/2015 |

OTHER PUBLICATIONS

Bala, M., et al., "Novel Peptidominics as Angiotensin-Converting Enzyme Inhibitors: A Combinatorial Approach," Bioorganic and Medicinal Chemistry, 10(11): 3685-3691 (Nov. 2002).
Barltrop, J.A., et al., "The Chemistry of 1,2-Dithiolane (Trimethylene Disulfide) as a Model for the Primary Quantum Conversion Act in Photosysthesis", JACS, 76:4348-4367 (1954).
Bartzatt, R.L., "Utilizing a D-Amino Acid as a Drug Carrier for Antineoplastic Nitrogen Mustard Groups," Drug Delivery, 12(3): 141-147 (2005), abstract only.
Bastin, R.J., et al., "Salt Selection and Optimisation Procedures for Pharmaceutical New Chemical Entities," Organic Process Res. And Dev., 427-435 (2000).
Berg, T., et al. Biochemistry Fifth Edition, pp. 43, 467 and 468 (2001).
Bessalle, R. et al., "All-D-magainin: Chirality, Antimicrobial Activity and Proteolytic Resistance," FEBS Lett., 274(1, 2): 151-155 (Nov. 1990).
Biewenga, G., et al., "The Pharmacology of the Antioxidant Lipoic Acid," Gen. Pharmac., 29(3): 315-331 (1997).
Bilska, A., et al., "Lipoic Acid—the Drug of the Future," Pharmacological Reports, 57(5): 570-577 (Jan. 2005).

Branden, C. and Tooze, J., Introduction to Protein Structure $2^{nd}$. Ed. pp. 4-5 (1999).
Brown, P.R., "Effect of Solvent on the Photolysis of α-Lipoic Acid", JOC, 34:3131-3135 (1969).
Bunjes, N., et al., "Thiopeptide-Supported Lipid Layers on Solid Substrates," Langmuir, 13:6188-6194 (1997).
Cacciatore, I. et al., "®-α-Lipoyl-Gylcyl-L-Prolyl-L-Glutamyl Dimethyl Ester Codrug as a Multifunctional Agent with Potential Neuroprotective Activities," ChemMedChem, vol. 7; 2021-2029 (2012).
CAPLUS Accession No. 2006-1007709, CAS abstract for Kates WO 2006101909, published 2006.
CAPLUS Accession No. 2008: 1371872, published 2008.
CAS display of compounds in WO 2006/101909, published Sep. 28, 2006 and entitled "Combination Therapy for Treating and Preventing Diseases."
Chemical Abstract Service Job Listing for Scientific Information Analysis, Retrieved from internet on Oct. 20, 2010: https://jobs.cas.org/epostings/submit.cfm?fuseaction=app.jobinfo[insert ampersand]jobid=205158[insert ampersand]compa.
Chemical Abstract Service, Job Listing for Part-Time Organic Chemistry, Retrieved from internet on Oct. 20, 2010: https://jobs.cas.org/epostings/submit.cfm?fuseaction=app.jobinfo[insert ampersand]id=23[insert ampersand]jobid=205101.
Chen, S. et al., "Salidroside Improves Behavioral and Histological Outcomes and Reduces Apoptosis via P13K/Akt Signaling after Experimental Traumatic Brain Injury," PLOS, vol. 7; No. 9; e45763; 15 pages (2012).
Clever Approach May Provide New Clues to Drug Design, Retrieved from Internet on Dec. 9, 2010: http://www.wi.mit.edu/scripts/pfl.php?p=http:/www.wi.mit.edu/news/archives/1996/pk_0[insert 3 periods], 2 pages.
Creighton, T.E., "The Polymeric Nature of Proteins", In Proteins: Structures and Molecular Properties, 2nd Edition, Creighton, T.E. ed. (NY: W.H. Freeman and Company) p. 2 (1984).
Development and Uses of Alitame: A Novel Dipeptide Amide Sweetener, Glowaky, R.C. et al., Abstract only, Retrieved from Internet on Nov. 19, 2010: http://pubs.acs.org/doi/abs/10.1021/bk-1991-0450.ch005.
Diesel, B., et al., Biochemistry 46: 2146-2155 (2007).
Fields, G.B. and Noble, R.L., "Solid Phase Peptide Synthesis Utilizing 9-Fluorenylmethosycarbonyl Amino Acids," Int. J. Peptide Protein Res. 35: 161-214 (1990).
Final Office Action for U.S. Appl. No. 14/710,074, entitled: "Formulations Comprising Lipoyl Compounds", dated Nov. 25, 2016.
Final Office Action for U.S. Appl. No. 12/466,170, "Compositions And Methods for Treating Ischemia And Ischemia-Reperfusion Injury", dated Oct. 23, 2009.
Greve, M.W. and Zink, B.J., "Pathophysiology of Traumatic Brain Injury," Mount Sinai Journal of Medicine, vol. 76; 97-104 (2009).
Guillonneau, C., et al., "Synthesis and pharmacological evaluation of new 1,2-dithiolane based antioxidants", Eur. J. Med. Chem., 38:1-11 (2003).
Hagen, T.M., et al., "(R)-alpha-Lipoic Acid Reverses the Age-Associasted Increase in Susceptibility of Hepatocytes to tert-Butylhydroperoxide Both In Vitro and In Vivo," Antioxidants and Redox Signaling, 2(3): 473-486 (2000).
Hall, E.D., "Chapter 11 Translational Principles of Neuroprotective and Neurorestorative Therapy Testing in Animal Models of Traumatic Brain Injury," NCBI, https://www.ncbi.nlm.nih.gov/books/NBK326712/?report=printable, 21 pages, (2016).
Hardesty, J.O., et al., "Enzymatic Proteolysis of a Surface-Bound α-Helical Polypeptide," Langmuir 24: 13944-13956 (2008).
Holmquist, L., et al., "Lipoic Acid as a Novel Treatment for Alzheimer's Disease and Related Dementias," Pharmacology and Therapeutics, 113: 154-164 (2007).
International Preliminary Report on Patentability for PCT/US2014/000090, "Formulations Comprising Lipoyl Compounds", dated Nov. 24, 2016.
International Preliminary Report on Patentability for PCT/US2010/034701, "Compositions And Methods For Treating Ischemia And Ischemia-Reperfusion Injury", dated Nov. 15, 2011.

(56) References Cited

OTHER PUBLICATIONS

International Search Report and Written Opinion, for PCT/US2014/000090, entitled "Compositions And Methods For Treating Ischemia And Ischemia-Reperfusion Injury", dated Jul. 31, 2014.
International Search Report and Written Opinion, PCT/US2011/060259, "Lipoyl Compounds and Their Use for Treating Ischemic Injury", dated Jan. 27, 2012.
Izutsu, K.-i., "Stabilization of Therapeutic Proteins by Chemical and Physical Methods" in Therapeutic Proteins Methods and Protocols, Molecular Biology 308, C.M. Smales, et al. eds. (NJ: Human Press), pp. 287-292 (2005).
Jia, L., et al., "Protective Effect of Lipoic Acid Against Acrolein-Induced Cytotoxicity in IMR-90 Human Fibroblasts," J. Nutr. Sci. Vitaminol., 55: 126-130 (2009).
Kates, S.A. et al., "Lipoic acid analogs with enhanced pharmacological activity," Bioorganic & Medicinal Chemistry, vol. 22; 505-512 (2014).
Khoronenkova, S.V. and Tishkov, V.I., "D-Amino Oxidase: Physiological Role and Applications", Biochemistry, 73(13):1511-1518 (2008).
Kilbaugh et al., "CMX-2043 Improves Outcomes Following Focal Traumatic Brain Injury in a Randomized Placebo Controlled Pre-Clinical Efficacy Trial;" The Third Joint Symposium of the International and National Neurotrauma Societies and AANS/CNS Section on Neurotrauma and Critical Care; Aug. 11-16, 2018; Toronto, Canada.
Kilic, F., et al., "Modelling Cortical Cataractogenesis XX. In Vitro Effect of Alpha-Lipoic Acid on Glutathione Concentrations in Lens in Model Diabetic Cataractogenesis," Biochemistry and Molecular Biology International, 46(3): 585-595 (Oct. 1998).
Metabolism of Nitrogen-Containing Compounds. Biochemistry, Zubay, p. 592, Table 24.2 (1998).
Morales, et al., "Experimental Models of Traumatic Brain Injury: Do We Really Need To Build A Better Mousetrap?", Neuroscience, 136:971-989 (2005).
Narayan, R.K., "Clinical Trials in Head Injury," J. Neurotrauma, 19(5):503-557 (May 2002).
Nomenclature Policy: Abbreviated Designations of Amino Acids, Am. J. Clin. Nutr., 47, 589 (1988).
Nomenclature Policy: Generic Descriptors and Trivial Names for Vitamins and Related Compounds, Am. J. Clin. Nutr., 47, 581-588 (1988).
Non-Final Office Action for U.S. Appl. No. 14/918,175, entitled: "Compositions And Methods For Treating Ischemia And Ischemia-Reperfusion Injury"; dated Aug. 29, 2016.
Notice of Allowance for U.S. Appl. No. 12/466,170, "Compositions And Methods for Treating Ischemia And Ischemia-Reperfusion Injury", dated Mar. 2, 2011.
Notice of Allowance for U.S. Appl. No. 13/041,001, "Compositions And Methods For Treating Ischemia And Ischemia-Reperfusion Injury", dated Feb. 25, 2014.
Notice of Allowance for U.S. Appl. No. 13/319,839, "Compositions And Methods For Treating Ischemia And Ischemia-Reperfusion Injury", dated Mar. 10, 2014.
Notice of Allowance for U.S. Appl. No. 13/885,289, "Lipoyl Compounds and Their Use for Treating Ischemic Injury", dated Jun. 14, 2014.
Notice of Allowance for U.S. Appl. No. 14/918,175, entitled: "Compositions and Methods for Treating Ischemia and Ischemis-Reperfusion Injury", dated Nov. 23, 2016.
Notice of Allowance for U.S. Appl. No. 14/456,646, "Lipoyl Compounds And Methods For Treating Ischemic Injury", dated Mar. 16, 2016.
Notice of Allowance for U.S. Appl. No. 15/962,575, dated Apr. 14, 2020.
Notification Concerning Transmittal of International Preliminary Report on Patentability and Written Opinion for PCT/US2011/060259, "Lipoyl Compounds and Their Use for Treating Ischemic Injury", dated May 30, 2013.
Notification Concerning Transmittal of International Preliminary Report on Patentability, "Compositions And Methods For Treating Traumatic Brain Injury," PCT/US2018/029372, dated Nov. 7, 2019.
Notification of Transmittal of the International Search Report and the Written Opinion of the International Searching Authority for Int'l Application No. PCT/US2010/034701 "Compositions And Methods For Treating Ischemia And Ischemia-Reperfusion Injury.", dated Jul. 15, 2010.
Notification of Transmittal of the International Search Report and the Written Opinion for International Application No. PCT/US2018/029372, entitled: "Compositions And Methods For Treating Traumatic Brain Injury," dated Jun. 27, 2018.
NovaBiochem. Catalog and Peptide Synthesis Handbook pp. x, xi, 1, 2, 18, 19 (1999).
Office Action for U.S. Appl. No. 13/041,001, "Compositions And Methods For Treating Ischemia And Ischemia-Reperfusion Injury", dated Nov. 4, 2013.
Office Action for U.S. Appl. No. 13/319,839, "Compositions And Methods For Treating Ischemia And Ischemia-Reperfusion Injury.", dated Nov. 1, 2013.
Office Action dated Jul. 22, 2009 for U.S. Appl. No. 12/466,170, entitled "Compositions And Methods For Treating Ischemia And Ischemia-Reperfusion Injury".
Office Action for U.S. Appl. No. 13/885,289, "Lipoyl Compounds and Their Use for Treating Ischemic Injury", dated Feb. 28, 2014.
Office Action for U.S. Appl. No. 14/283,844, "Compositions And Methods For Treating Ischemia And Ischemia-Reperfusion Injury", dated Apr. 21, 2015.
Office Action for U.S. Appl. No. 14/456,646, "Lipoyl Compounds And Methods For Treating Ischemic Injury", dated Jul. 21, 2015.
Office Action for U.S. Appl. No. 14/710,074, "Formulations Comprising Lipoyl Compounds", dated Jul. 6, 2016.
Office Action for U.S. Appl. No. 15/962,575, dated Aug. 23, 2019.
Packer, L., et al., "Molecular Aspects of Lipoic Acid in the Prevention of Diabetes Complications," Nutrition, 17: 888-895 (2001).
Panigrahi, M., "[Alpha]-Lipoic Acid Protects Against Reperfusion Injury Following Cerebral Ischemia in Rats," Brain Research, 717(1-2): 184-188 (Apr. 1996).
Pick, U., et al., "Glutathione Reductase and Lipoamide Dehydrogenase Have Opposite Stereospecficities for α-Lipoic Acid Enantiomers," Biochem. and Biophys. Res. Comm. 206(2): 724-730 (Jan. 1995).
Rosini, M., et al., Rational Approach to Discover Multipotent Anti-Alzheimer Drugs, J. Med. Chem, 48(20):360-363 (2005).
Sato, et al., "Dihydroxyindole polymerization inhibitors, and their use for topical formulations inhibiting," STN International HCAPLUS database, Accession No. 2006:74266 (2006).
Sehirli, O., et al., "α-Lipoic Acid Protects Against Renal Ischaemia-Reperfusion Injury in Rats," Clin. Exp. Pharmacol. Phys., 35: 249-255 (2008).
Sela, M. and Zisman, E., "Different Roles of D-Amino Acids in Immune Phenomena," The FASEB Journal, 11: 449 (1997).
Sigma Peptides and Amino Acids Catalog, cover page, pp. 143-144 (1995).
Smith, J.R., et al., "Differential Activity of Lipoic Acid Enantiomers in Cell Culture," Journal of Herbal Pharmacotherapy, 5(3): 43-54 (2005).
Statler, et al., "The Simple Model Versus the Super Model: Translating Experimental Traumatic Brain Injury Research to the Bedside," J. Neurotrauma, 18(11):1195-1206, (2001).
STN Tokyo, International, L-Alanine, N-[5-(3R)-1,2-dithiolan-3-yl-1-oxopentyl]-L-beta-glutamyl-, file Registry [online], uploaded on Oct. 18, 2006, [searched on Jun. 6, 2013], CAS Registry No. 910627-26-8.
Thomas, R.C., et al., "Disulfide Polymers of DL-α-Lipoic Acid", JACS, 78:6148-6149 (1956).
Van der Meijden, M.W. et al., "Attrition-Enhanced Deracemization in the Synthesis of Clopidogrel—A Practical Application of a New Discovery," Organic Process Research and Development 13: 1195-1198 (2009).
Wagner, et al., "Properties and Derivatives of α-Lipoic Acid", JACS, 78:5079-5081 (1956).
Whiteman M., et al., FEBS Letters 379: 74-76 (1996).

(56) References Cited

OTHER PUBLICATIONS

Wolz, P. and Krieglstein, J., "Neuroprotective Effects of α-Lipoic Acid and Its Enantiomers Demonstrated in Rodent Models of Focal Cerebral Ischemia," Neuropharmacology, 35(3): 369-375 (1996).

Xiong, et al., "Animal models of traumatic brain injury," Nature, 14:128-142, (Feb. 2013).

Yu, G.L., et al., "Montelukast, a Cysteinyl Leukotriene Receptor-1 Antagonist, Dose- and Time-Dependently Protects against Focal Cerebral Ischemia in Mice," Pharmacology 73:31-40 (2005).

Ziegler, D., et al., "Treatment of symptomatic diabetic polyneuropathy with the antioxidant α-lipoic acid: a meta-analysis", Diabetic Medicine, 21:114-121 (2004).

Zimmer, G., et al., "Dose/Response Curves of Lipoic Acid R- and S-Forms in the Working Rat Heart During Reoxygenation: Superiority of the R-Enantiomer of Enhancement of Aortic Flow," J. Mol. Cell. Cardiol. 27: 1895-1903 (1995).

Zimmer, R., et al., "Enantioselective Synthesis of (S)- and (R)-6-Hydroxy-8-nonenecarboxylates by Asymmetric Catalysis: A Formal Synthesis of (R)-α-Lipoic Acid and Its (S)-Antipode," Tetrahedron: Asymmetry, 11:879-887 (2000).

* cited by examiner

*P<0.05 indicates a significant difference from saline treated animals.

*P<0.05 indicates a significant difference from saline treated animals.

COMPOSITIONS AND METHODS FOR TREATING TRAUMATIC BRAIN INJURY

RELATED APPLICATION

This application is a Continuation of U.S. application Ser. No. 15/962,575, filed on Apr. 25, 2018, which claims the benefit of U.S. Provisional Application No. 62/489,735, filed on Apr. 25, 2017. The entire teachings of these applications are incorporated herein by reference.

BACKGROUND OF THE INVENTION

Traumatic brain injury (TBI) is caused by a physical impact or other trauma that damages the brain. Depending on the source of the trauma, the resulting impact can cause an open head or a closed head injury. Open head injuries are typically caused by penetrating objects (e.g., a bullet or other projectile). Closed head injuries are often caused by blunt force trauma, such as the head hitting a windshield during a car accident. In both open and closed head injuries, there is immediate, primary damage to the brain (such as brain bleeding), followed by secondary brain damage (such as increased pressure within the skull and seizures) that evolves over time. Secondary brain damage sometimes affects the hippocampus region of the brain, which is involved in learning and memory. Secondary brain damage after a TBI can also affect cognitive, behavior and sensorimotor function to varying degrees.

Treatments for TBI vary based on the type and the severity of the injury. Surgery is sometimes needed to address primary brain damage and to stabilize a patient's condition. Acute treatment can sometimes be offered to minimize secondary damage, but such treatments tend to be palliative. For example, a patient may be administered sedating medications to induce a coma that will reduce the patient's agitation and facilitate healing. Medications to reduce spasticity may also be used as the patient recovers function. Other drugs may be used to assist with attention and concentration problems (including, for example, amantadine, methylphenidate, bromocriptine and antidepressants) or to subdue aggressive behavior (including, for example, carbamamazapine and amitriptyline). However, there are few effective drugs that directly treat or protect the brain from secondary brain damage.

Given the widespread incidence and lack of effective treatment options, there remains a significant unmet medical need to identify new methods for treating or preventing brain damage (e.g., secondary brain damage) caused by TBI.

SUMMARY OF THE INVENTION

The invention described herein addresses the medical need for new methods for treating and/or preventing TBI, including secondary brain damage caused by TBI, by providing, e.g., methods targeting the secondary cascade of neurodegenerative damage caused by traumatic brain injury and improving long term functional outcomes associated with cognitive, behavior and sensorimotor function following a traumatic brain injury.

In an embodiment, the invention provides methods for treating and/or preventing TBI (e.g., treating or preventing neurodegenerative damage caused by a traumatic brain injury; improving functional outcomes associated with cognitive, behavior and/or sensorimotor function following a traumatic brain injury) in a subject in need thereof. The methods of the invention comprise, in certain embodiments, administering to a subject in need thereof an effective amount of a compound represented by Structural Formula I:

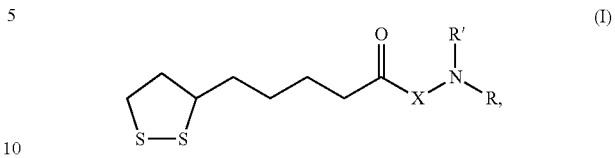

or a pharmaceutically acceptable salt or prodrug thereof, wherein:

R is $(C_1-C_{18})$alkyl, $(C_6-C_{18})$aryl or $(C_6-C_{18})$aryl$(C_1-C_{18})$alkyl and is substituted with at least one acidic substituent selected from the group consisting of —$CO_2H$, —$SO_3H$, —$PO_3H_2$, —$OSO_3H$, —$OPO_3H_2$, —$B(OH)_2$ and —NHOH, wherein the aryl of the $(C_6-C_{18})$aryl or $(C_6-C_{18})$aryl$(C_1-C_{18})$alkyl is optionally further substituted with one or more substituents selected from the group consisting of hydroxy, halo, $(C_1-C_3)$alkyl, halo$(C_1-C_3)$alkyl, cyano, nitro, $(C_1-C_3)$alkoxy and thio$(C_1C_3)$alkyl;

R' is hydrogen or $(C_1-C_{18})$alkyl, wherein $(C_1-C_{18})$alkyl is optionally substituted with one or more acidic substituents selected from the group consisting of —$CO_2H$, —$SO_3H$, —$PO_3H_2$, —$OSO_3H$, —$OPO_3H_2$, —$B(OH)_2$ and —NHOH; and X is absent or is an amino acid, wherein the amino acid is oriented to form an amide linkage with

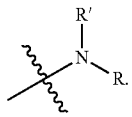

The present invention also provides, in various embodiments, compositions for use in treating and/or preventing TBI in a subject in need thereof, compounds for use in the manufacture of a medicament for treating and/or preventing TBI in a subject in need thereof, and methods of preparing a pharmaceutical composition for treating and/or preventing secondary brain damage caused by TBI. Thus, an embodiment of the present invention is a compound represented by Structural Formula (I), or a pharmaceutically acceptable salt or prodrug thereof, for use in treating and/or preventing (e.g., treating) TBI. Another embodiment of the present invention is use of a compound represented by Structural Formula (I), or a pharmaceutically acceptable salt or prodrug thereof, for the manufacture of a medicament for treating and/or preventing (e.g., treating) TBI.

The lipoyl compounds of Structural Formulas (I), (Ia), (II) and (IIa) (also referred to herein as "the disclosed compounds"), compositions and methods of the present invention are efficacious for treating TBI, including secondary brain damage caused by TBI and/or long term functional outcomes associated with cognitive, behavior and sensorimotor function following TBI.

DETAILED DESCRIPTION OF THE INVENTION

Figure 1:
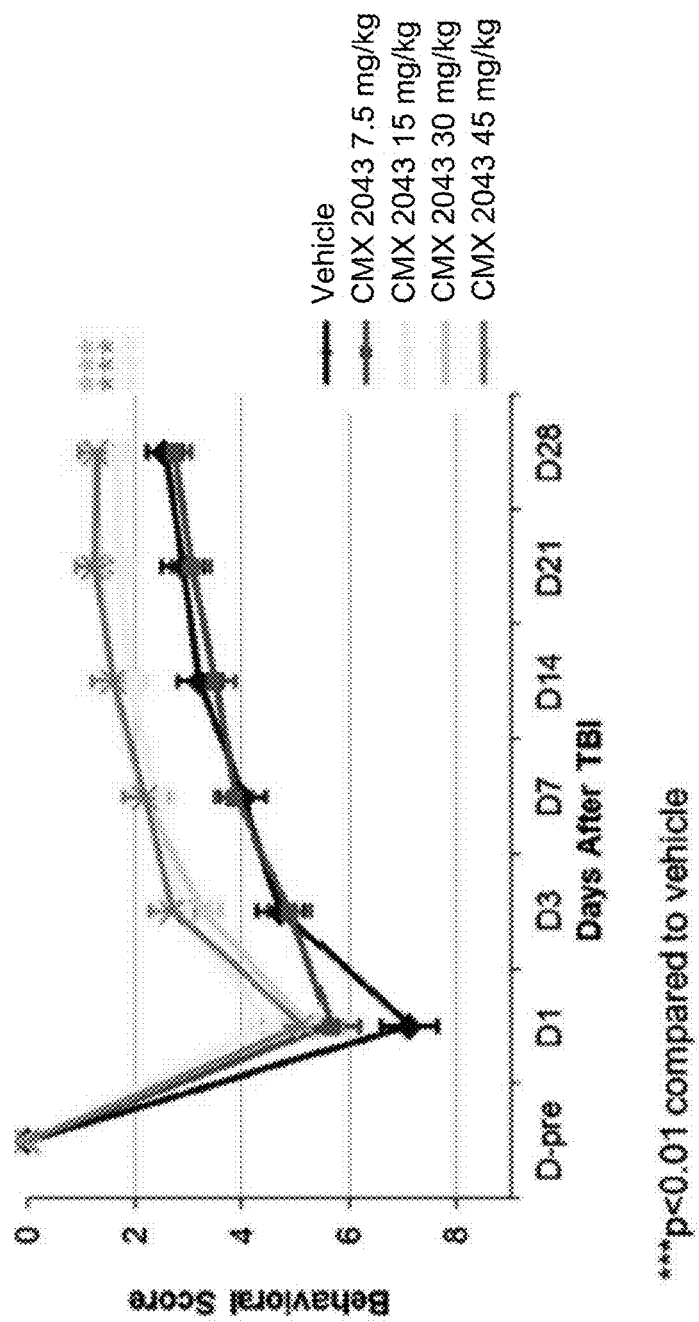
FIG. 1 shows the results of a limb placing test in rats following treatment with different doses of the compound N—(R)-lipoyl-glutamylalanine (RLip-Glu-Ala, also designated herein as CMX-2043) in a fluid percussion model of diffused traumatic brain injury (TBI). ***P<0.01 indicates a significant difference from saline treated animals.

A description of example embodiments of the invention follows.

The present invention generally relates to compounds, compositions and methods for preventing and/or treating TBI in a subject in need thereof using neuroprotective lipoyl compounds described herein. As used herein, "treating TBI" includes treating neurodegenerative damage (e.g., the secondary cascade of neurodegenerative damage) caused by traumatic brain injury, as well as improving long term functional outcomes (e.g., outcomes associated with cognitive, behavior and sensorimotor function) following a traumatic brain injury.

In order that the invention may be better understood, the following terms are defined as follows:

Compounds useful in the methods of the invention can exist in various stereoisomeric forms or mixtures thereof unless otherwise specified. "Stereoisomers" are compounds that differ only in their spatial arrangement. "Enantiomers" are pairs of stereoisomers that are non-superimposable mirror images of one another, most commonly because they contain an asymmetrically substituted carbon atom that acts as a chiral center.

"Diastereomers" are stereoisomers that are not related as mirror images, most commonly because they contain two or more asymmetrically substituted carbon atoms. "R" and "S" represent the configuration of substituents around one or more chiral carbon atoms.

"Racemate" or "racemic mixture," as used herein, refers to a mixture containing equimolar quantities of two enantiomers of a compound. Such mixtures exhibit no optical activity (i.e., they do not rotate a plane of polarized light).

Percent enantiomeric excess (ee) is defined as the absolute difference between the mole fraction of each enantiomer multiplied by 100% and can be represented by the following equation:

$$ee = \left| \frac{R-S}{R+S} \right| \times 100\%,$$

where R and S represent the respective fractions of each enantiomer in a mixture, such that R+S=1. When a single enantiomer is named or depicted by structure, the depicted or named enantiomer is present in an ee of at least or about 50%, about 60%, about 70%, about 80%, about 90%, about 95%, about 98%, about 99% or about 99.9%.

Percent diastereomeric excess (de) is defined as the absolute difference between the mole fraction of each diastereomer multiplied by 100% and can be represented by the following equation:

$$de = \left| \frac{D1 - (D2+D3+D4\ldots)}{D1 + (D2+D3+D4\ldots)} \right| \times 100\%,$$

where D1 and (D2+D3+D4 . . . ) represent the respective fractions of each diastereomer in a mixture, such that D1+(D2+D3+D4 . . . )=1. When a single diastereomer is named or depicted by structure, the depicted or named diastereomer is present in a de of at least or about 50%, about 60%, about 70%, about 80%, about 90%, about 95%, about 98%, about 99% or about 99.9%.

When a disclosed compound is named or depicted by structure without indicating the stereochemistry, and the compound has one chiral center, it is to be understood that the name or structure encompasses one enantiomer of the compound substantially separated from the corresponding optical isomer, a racemic mixture of the compound and mixtures enriched in one enantiomer relative to its corresponding optical isomer.

When a disclosed compound is named or depicted by structure without indicating the stereochemistry and has two or more chiral centers, it is to be understood that the name or structure encompasses a diastereomer substantially separated from other diastereomers, a pair of diastereomers substantially separated from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

"(R)-Lipoyl" refers to a compound containing a lipoyl moiety, wherein the stereocenter in the lipoyl moiety is in the (R) configuration. An (R)-lipoyl moiety is pictured below:

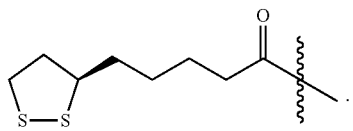 [SMILES: *C(=O)CCCC[C@@H]1CCSS1]

An example of an (R)-lipoyl compound is shown below:

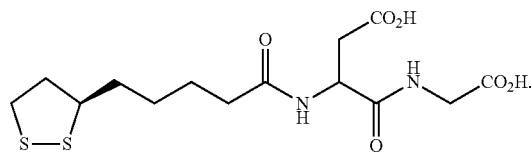 [SMILES: O=C(O)CNC(=O)C(CC(=O)O)NC(=O)CCCC[C@@H]1CCSS1]

In one embodiment of this invention, the (R)-lipoyl stereoisomer is separated from the (S)-lipolyl steriosomer of a compound having Structural Formula (I) for use in the methods of this invention.

"(S)-Lipoyl" refers to a compound containing a lipoyl moiety, wherein the stereocenter in the lipoyl moiety is in the (S) configuration. An (S)-lipoyl moiety is pictured below:

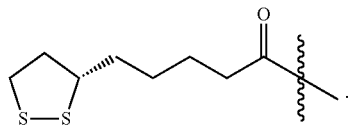 [SMILES: *C(=O)CCCC[C@H]1CCSS1]

An example of an (S)-lipoyl compound is shown below:

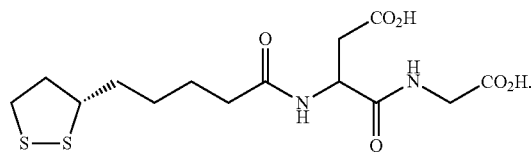 [SMILES: O=C(O)CNC(=O)C(CC(=O)O)NC(=O)CCCC[C@H]1CCSS1]

In one embodiment of this invention, the (S)-lipoyl stereoisomer is separated from the (R)-lipolyl steriosomer of a compound having Structural Formula (I) for use in the methods of this invention.

"Alkyl" means a saturated aliphatic branched or straight-chain monovalent hydrocarbon radical having the specified number of carbon atoms. Thus, "$(C_1-C_6)$alkyl" means a radical having from 1-6 carbon atoms in a linear or branched arrangement. "$(C_1-C_6)$alkyl" includes methyl, ethyl, propyl, i-propyl, butyl, i-butyl, t-butyl, sec-butyl, pentyl and hexyl. Typically, alkyl has 1 to 20, 1 to 15, 1 to 10, 1 to 5 or 1 to 3 carbon atoms.

The term "alkoxy" means —O-alkyl, where alkyl is as defined above.

The term "halogen" means F, Cl, Br or I.

The term "aryl" means a carbocyclic aromatic ring. "$(C_6-C_{14})$aryl" includes phenyl, napthyl, indenyl, and anthracenyl. Typically, aryl has 6 to 20, 6 to 14, 6 to 10, 6 to 9, or 6 carbon atoms.

As used herein, "substantially separated" or "substantially pure" means that the ee or de of the depicted or named compound is at least about 50%. For example, "substantially separated" or "substantially pure" can mean the ee or de of the depicted or named enantiomer is at least or about 50%, about 60%, about 70%, about 80%, about 90%, about 95%, about 98%, about 99% or about 99.9%. In one embodiment, substantially separated or substantially pure means that the ee or de of the depicted or named compound is at least or about 75%. In a specific embodiment, substantially separated means that the ee or de of the depicted or named compound is at least or about 90%. In a more specific embodiment, substantially separated means that the ee or de of the depicted or named compound is at least or about 95%. In yet a more specific embodiment, substantially separated means that the ee or de of the depicted or named compound is at least or about 99%. In another specific embodiment, substantially separated means that the ee or de of the depicted or named compound is at least or about 99.9%.

As used herein, the term "amino acid" means a molecule containing an amine group, a carboxylic acid group and a side chain which varies between different amino acids and includes both naturally-occurring amino acids and non-naturally-occurring amino acids. In one embodiment, "amino acid" is used to refer to naturally-occurring amino acids.

As used herein, the term "naturally-occurring amino acid" means a compound represented by the formula $NH_2$—CHR—COOH, wherein R is the side chain of a naturally-occurring amino acid such as an amino acid listed or named in the Table below. "Naturally-occurring amino acid" includes both the d- and l-configuration. When an amino acid is named or depicted by structure without indicating the stereochemistry and has at least one chiral center, it is to be understood that the name or structure encompasses a single enantiomer or diastereomer substantially separated from the other enantiomer or diastereomer, in which the one enantiomer or diastereomer is enriched relative to the other enantiomer or diastereomer(s), a racemic or diastereomeric mixture of the enantiomer or diastereomer(s) and mixtures enriched in one enantiomer or diastereomer relative to its corresponding optical isomer or other diastereomer(s).

| Table of Common Naturally Occurring Amino Acids | | |
|---|---|---|
| Amino acid | Three letter code | One letter code |
| Non-polar; neutral at pH 7.4 | | |
| Alanine | Ala | A |
| isoleucine | Ile | I |
| Leucine | Leu | L |
| methionine | Met | M |
| phenylalanine | Phe | F |
| Proline | Pro | P |

-continued

Table of Common Naturally Occurring Amino Acids

| | Amino acid | Three letter code | One letter code |
|---|---|---|---|
| | tryptophan | Trp | W |
| | Valine | Val | V |
| Polar, | asparagine | Asn | N |
| uncharged | Cysteine | Cys | C |
| at pH 7.0 | Glycine | Gly | G |
| | glutamine | Gln | Q |
| | Serine | Ser | S |
| | threonine | Thr | T |
| | Tyrosine | Tyr | Y |
| Polar; | glutamic acid | Glu | E |
| charged | Arginine | Arg | R |
| at pH 7 | aspartic acid | Asp | D |
| | histidine | His | H |
| | Lysine | Lys | K |

"Non-natural amino acid" means an amino acid for which there is no nucleic acid codon. Examples of non-natural amino acids include natural α-amino acids with non-natural side chains; β-amino acids (e.g., β-alanine); and γ-amino acids (e.g., γ-aminobutryric acid).

As used herein, an "effective amount" is an amount sufficient to achieve a desired therapeutic or prophylactic effect in a subject in need thereof under the conditions of administration, such as, for example, an amount sufficient to treat or inhibit (e.g., prevent or delay) secondary brain damage from (e.g., consequent to) a TBI. The effectiveness of a therapy can be determined by suitable methods known by those of skill in the art. An effective amount includes any amount of a compound (e.g., a compound of Structural Formula (I)) which prevents the onset of, alleviates the symptoms of, stops the progression of the condition, disorder or disease being treated and/or promotes improvement in long term functional outcomes (e.g., secondary brain damage due to a TBI) in a subject.

The term "treating" is defined herein as administering to a subject in need thereof an effective amount of a compound (e.g., of Structural Formula (I), or a pharmaceutically acceptable salt or prodrug thereof) that is sufficient to prevent the onset of, alleviate the symptoms of, or stop the progression of a condition, disorder or disease being treated.

The term "subject," as used herein, refers to a mammal. In a particular embodiment, the subject is a human.

The term "subject in need thereof," refers to a subject that has sustained, or is at risk for sustaining, a TBI.

"Effective amount" refers to the amount of a compound that will elicit the biological or medical response of a cell, tissue, system, animal, mammal, or human that is being sought by the researcher, veterinarian, medical doctor or other clinician. An effective amount may be in the range of 0.001 mg/kg to 1000 mg/kg. An effective amount may also be in the range of 0.1 mg/kg to 100 mg/kg. An effective amount may also be in the range of 1 mg/kg to 20 mg/kg. An effective amount can be administered as acute, subacute or chronic regimen, as required to achieve the desired outcome.

The methods of the present invention are particularly useful for preventing and/or treating the secondary cascade of neurodegenerative damage caused by TBI, and/or improving functional outcomes associated with cognitive, behavior and sensorimotor function following TBI. The secondary cascade of neurodegenerative damage may be associated with a focal or diffused traumatic brain injury. In one embodiment, the TBI is caused by blunt force trauma, blast impact or excessive acceleration and/or deceleration. Blunt force trauma causing TBI is a severe traumatic episode caused by the sudden impact of a blunt instrument to the head. Blunt force trauma can be experienced during a car accident following impact with any part of the car (for example, the dashboard, steering wheel, the rear of the driver or passenger side seats or the windshield). Blunt force trauma can also be caused by an attack against a victim using a fist, a piece of wood, baseball bat or other item that would cause such an injury. Blast injury may result from, for example, exposure to primary blast waves with or without a direct blow to the head following detonation of an explosive device (e.g., bomb or an improvised explosive device (IED)). Acceleration and deceleration injuries result from the abrupt movement and deformation of the brain in the cranial cavity following a sudden acceleration or abrupt deceleration of skull movement. Such injuries are common in motor vehicle accidents or other incidents that cause whiplash-type injuries.

The methods of the present invention are also particularly well suited for treating concussion injuries, including for example, multiple concussion injuries experienced in high impact sports. Accordingly, provided herein are methods for treating a concussion injury in a subject which/who has sustained a concussion injury, comprising administering to the subject an effective amount of a compound disclosed herein (e.g., a compound of Structural Formula (I), or a pharmaceutically acceptable salt or prodrug thereof).

The methods of the present invention may also be particularly well suited for treating and preventing damage to the hippocampus region of the brain following TBI. This type of secondary brain damage can be devastating to a TBI patient, as the hippocampus is integrally involved in learning and memory. The compounds used in the methods of this invention may help to preserve critical brain function and restore or enhance a patient's ability to learn and remember following a TBI (e.g., through neuroprotective effects). Accordingly, provided herein are methods for treating and/or preventing damage to the hippocampus region of the brain of a subject following TBI, comprising administering to the subject an effective amount of a compound disclosed herein (e.g., a compound of Structural Formula (I), or a pharmaceutically acceptable salt or prodrug thereof). Also provided herein are methods for preserving critical brain function and/or restoring or enhancing a subject's ability to learn and remember following TBI, comprising administering to the subject an effective amount of a compound disclosed herein (e.g., a compound of Structural Formula (I), or a pharmaceutically acceptable salt or prodrug thereof).

In addition, as described in the Examples herein, the methods of the invention have been shown to provide a therapeutic benefit leading to cognitive, behavior and sensorimotor improvements following a TBI in an animal model of TBI. Accordingly, the methods of this invention may be used to promote cognitive, behavior and sensorimotor recovery in a patient suffering from a TBI. Thus, also provided herein are methods for promoting cognitive, behavior and sensorimotor recovery in a subject suffering from TBI, comprising administering to the subject an effective amount of a compound disclosed herein (e.g., a compound of Structural Formula (I), or a pharmaceutically acceptable salt or prodrug thereof). In one embodiment, the method is a method for promoting cognitive recovery in a subject suffering from TBI, comprising administering to the subject an effective amount of a compound disclosed herein (e.g., a compound of Structural Formula (I), or a pharmaceutically acceptable salt or prodrug thereof). In another embodiment, the method is a method for promoting behavior recovery in a subject suffering from TBI, comprising administering to the subject an effective amount of a compound disclosed herein (e.g., a compound of Structural Formula (I), or a pharmaceutically acceptable salt or prodrug thereof). In yet another embodiment, the method is a method for promoting sensorimotor recovery in a subject suffering from TBI, comprising administering to the subject an effective amount of a compound disclosed herein (e.g., a compound of Structural Formula (I), or a pharmaceutically acceptable salt or prodrug thereof).

The present invention relates, in one embodiment, to a method for treating and/or preventing (e.g., treating) TBI (e.g., by treating the secondary cascade of neurodegenerative damage caused by TBI and/or improving long term functional outcomes associated with cognitive, behavior and sensorimotor function caused by TBI) in a subject in need thereof, comprising administering to the subject an effective amount of a compound of Structural Formula (I), or a pharmaceutically acceptable salt or prodrug thereof (e.g., a pharmaceutically acceptable salt thereof). In some embodiments, the compound is represented by Structural Formula (Ia):

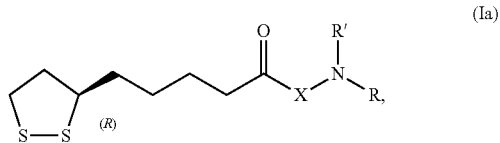

(Ia)

or a pharmaceutically acceptable salt or prodrug thereof.

R is $(C_1-C_{18})$alkyl, $(C_6-C_{18})$aryl or $(C_6-C_{18})$aryl$(C_1-C_{18})$alkyl and is substituted with at least one acidic substituent selected from the group consisting of —$CO_2H$, —$SO_3H$, —$PO_3H_2$, —$OSO_3H$, —$OPO_3H_2$, —$B(OH)_2$ and —NHOH, wherein the aryl of the $(C_6-C_{18})$aryl or $(C_6-C_{18})$aryl$(C_1-C_{18})$alkyl is optionally further substituted with one or more substituents selected from the group consisting of hydroxy, halo, $(C_1-C_3)$alkyl, halo$(C_1-C_3)$alkyl, cyano, nitro, $(C_1-C_3)$alkoxy and thio$(C_1-C_3)$alkyl.

In one embodiment, R is $(C_1-C_{18})$alkyl and is substituted with at least one acidic substituent selected from the group consisting of —$CO_2H$, —$SO_3H$, —$PO_3H_2$, —$OSO_3H$, —$OPO_3H_2$, —$B(OH)_2$ and —NHOH. In another embodiment, R is $(C_1-C_3)$alkyl and is substituted with at least one acidic substituent selected from the group consisting of —$CO_2H$, —$SO_3H$, —$PO_3H_2$, —$OSO_3H$, —$OPO_3H_2$, —$B(OH)_2$ and —NHOH. In a further embodiment, R is $(C_3)$alkyl and is substituted with at least one acidic substituent selected from the group consisting of —$CO_2H$, —$SO_3H$, —$PO_3H_2$, —$OSO_3H$, —$OPO_3H_2$, —$B(OH)_2$ and —NHOH. In a further embodiment, R is $(C_2)$alkyl and is substituted with at least one acidic substituent selected from the group consisting of —$CO_2H$, —$SO_3H$, —$PO_3H_2$, —$OSO_3H$, —$OPO_3H_2$, —$B(OH)_2$ and —NHOH. Alternatively, R is $(C_1)$alkyl and is substituted with at least one acidic substituent selected from the group consisting of —$CO_2H$, —$SO_3H$, —$PO_3H_2$, —$OSO_3H$, —$OPO_3H_2$, —$B(OH)_2$ and —NHOH.

In another embodiment, R is $(C_6-C_{18})$aryl and is substituted with at least one acidic substituent selected from the group consisting of —$CO_2H$, —$SO_3H$, —$PO_3H_2$, —$OSO_3H$, —$OPO_3H_2$, —$B(OH)_2$ and —NHOH, and is optionally further substituted with one or more substituents selected from the group consisting of hydroxy, halo, $(C_1-C_3)$alkyl, halo$(C_1-C_3)$alkyl, cyano, nitro, $(C_1-C_3)$alkoxy and thio$(C_1-C_3)$alkyl. In a further embodiment, R is $(C_6)$aryl and is substituted with at least one acidic substituent selected from the group consisting of —$CO_2H$, —$SO_3H$, —$PO_3H_2$, —$OSO_3H$, —$OPO_3H_2$, —$B(OH)_2$ and —NHOH, and is optionally further substituted with one or more substituents selected from the group consisting of hydroxy, halo, $(C_1-C_3)$alkyl, halo$(C_1-C_3)$alkyl, cyano, nitro, $(C_1-C_3)$alkoxy and thio$(C_1-C_3)$alkyl.

In another embodiment, R is $(C_6-C_{18})$aryl$(C_1-C_{18})$alkyl and is substituted with at least one acidic substituent selected from the group consisting of —$CO_2H$, —$SO_3H$, —$PO_3H_2$, —$OSO_3H$, —$OPO_3H_2$, —$B(OH)_2$ and —NHOH, wherein the aryl of the $(C_6-C_{18})$aryl$(C_1-C_{18})$alkyl is optionally further substituted with one or more substituents selected from the group consisting of hydroxy, halo, $(C_1-C_3)$alkyl, halo$(C_1-C_3)$alkyl, cyano, nitro, $(C_1-C_3)$alkoxy and thio$(C_1-C_3)$alkyl. In a further embodiment, R is $(C_6)$aryl$(C_1-C_3)$alkyl and is substituted with at least one acidic substituent selected from the group consisting of —$CO_2H$, —$SO_3H$, —$PO_3H_2$, —$OSO_3H$, —$OPO_3H_2$, —$B(OH)_2$ and —NHOH, wherein the aryl of the $(C_6)$aryl$(C_1-C_3)$alkyl is optionally further substituted with one or more substituents selected from the group consisting of hydroxy, halo, $(C_1-C_3)$alkyl, halo$(C_1-C_3)$alkyl, cyano, nitro, $(C_1-C_3)$alkoxy and thio$(C_1-C_3)$alkyl. Alternatively, R is $(C_6)$aryl$(C_1-C_2)$alkyl and is substituted with at least one acidic substituent selected from the group consisting of —$CO_2H$, —$SO_3H$, —$PO_3H_2$, —$OSO_3H$, —$OPO_3H_2$, —$B(OH)_2$ and —NHOH, wherein the aryl of the $(C_6)$aryl$(C_1-C_2)$alkyl is optionally further substituted with one or more substituents selected from the group consisting of hydroxy, halo, $(C_1-C_3)$alkyl, halo$(C_1-C_3)$alkyl, cyano, nitro, $(C_1-C_3)$alkoxy and thio$(C_1-C_3)$alkyl.

In another embodiment, R is $(C_6)$aryl$(C_2)$alkyl and is substituted with at least one acidic substituent selected from the group consisting of —$CO_2H$, —$SO_3H$, —$PO_3H_2$, —$OSO_3H$, —$OPO_3H_2$, —$B(OH)_2$ and —NHOH, wherein the aryl of the $(C_6)$aryl$(C_2)$alkyl is optionally further substituted with one or more substituents selected from the group consisting of hydroxy, halo, $(C_1-C_3)$alkyl, halo$(C_1-C_3)$alkyl, cyano, nitro, $(C_1-C_3)$alkoxy and thio$(C_1-C_3)$alkyl. In a further embodiment, R is $(C_6)$aryl$(C_1)$alkyl and is substituted with at least one acidic substituent selected from the group consisting of —$CO_2H$, —$SO_3H$, —$PO_3H_2$, —$OSO_3H$, —$OPO_3H_2$, —$B(OH)_2$ and —NHOH, wherein the aryl of the $(C_6)$aryl$(C_1)$alkyl is optionally further substituted with one or more substituents selected from the group consisting of hydroxy, halo, $(C_1-C_3)$alkyl, halo$(C_1-C_3)$alkyl, cyano, nitro, $(C_1-C_3)$alkoxy and thio$(C_1-C_3)$alkyl.

The at least one acidic substituent is selected from the group consisting of —$CO_2H$, —$SO_3H$, —$PO_3H_2$, —$OSO_3H$, —$OPO_3H_2$, —$B(OH)_2$ and —NHOH. In one embodiment, the at least one acidic substituent is selected from the group consisting of —$CO_2H$, —$SO_3H$, —$PO_3H_2$, —$OSO_3H$ and —$OPO_3H_2$.

R is substituted with at least one acidic substituent selected from the group consisting of —$CO_2H$, —$SO_3H$, —$PO_3H_2$, —$OSO_3H$, —$OPO_3H_2$, —$B(OH)_2$ and —NHOH. In one embodiment, R is substituted with one, two or three acidic substituents. In a further embodiment, R is substituted with one or two acidic substituents.

Aryl is optionally further substituted with one or more substituents selected from the group consisting of hydroxy, halo, $(C_1-C_3)$alkyl, halo$(C_1-C_3)$alkyl, cyano, nitro, $(C_1-C_3)$alkoxy and thio$(C_1-C_3)$alkyl. In one embodiment, aryl is further substituted with one, two or three substituents. In another embodiment, aryl is substituted with one substituent. Alternatively, aryl is unsubstituted. In a further embodiment, aryl is further substituted with one or more substituents selected from the group consisting of hydroxy or halo.

R' is hydrogen or $(C_1-C_{18})$alkyl, wherein said $(C_1-C_{18})$ alkyl is optionally substituted with one or more acidic substituents selected from the group consisting of $—CO_2H$, $—SO_3H$, $—PO_3H_2$, $—OSO_3H$, $—OPO_3H_2$, $—B(OH)_2$ and $—NHOH$. In one embodiment, R' is hydrogen.

In one embodiment, R' is $(C_1-C_{18})$alkyl. In another embodiment, R' is $(C_1-C_3)$alkyl. In a further embodiment, R' is $(C_3)$alkyl. In a further embodiment, R' is $(C_2)$alkyl. Alternatively, R' is $(C_1)$alkyl.

R' is substituted with at least one acidic substituent selected from the group consisting of $—CO_2H$, $—SO_3H$, $—PO_3H_2$, $—OSO_3H$, $—OPO_3H_2$, $—B(OH)_2$ and $—NHOH$. In one embodiment, R' is substituted with one, two or three acidic substituents. In another embodiment, R' is substituted with one or two acidic substituents. In a further embodiment, R' is substituted with one acidic substituent. Alternatively, R' is unsubstituted.

X is absent or an amino acid, wherein the amino acid is oriented to form an amide linkage with

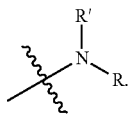

For example, the moiety in N-lipoyl-glutamylalanine is oriented as shown in the structural formula below:

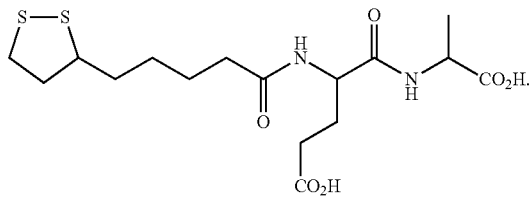

In one embodiment, X is absent. Alternatively, X is an amino acid. In a further embodiment, X is a naturally-occurring amino acid. In yet a further embodiment, X is aspartic acid, tyrosine, glutamic acid or alanine.

In a 1$^{st}$ specific embodiment, the compound is represented by Structural Formula (I) and/or (Ia), wherein the values and alternative values for the variables are as described above.

In a first aspect of the 1$^{st}$ specific embodiment of the present invention, the (R)-lipoyl stereoisomer of a compound represented by Structural Formulas (I) or (Ia) is substantially separated from the (S)-lipoyl stereoisomer(s). Values and alternative values for the remainder of the variables are as described above for Structural Formulas (I) or (Ia) or in the 1$^{st}$ specific embodiment.

In a second aspect of the 1$^{st}$ specific embodiment of the present invention, R' is H. Values and alternative values for the remainder of the variables are as described above for Structural Formulas (I) or (Ia) or in the 1$^{st}$ specific embodiment, or first aspect thereof.

In a third aspect of the 1$^{st}$ specific embodiment of the present invention, R' is H and X is a naturally-occurring amino acid. Values and alternative values for the remainder of the variables are as described above for Structural Formulas (I) or (Ia) or in the 1$^{st}$ specific embodiment, or first or second aspect thereof.

In a fourth aspect of the 1$^{st}$ specific embodiment of the present invention, R and R' are each $(C_1-C_3)$alkyl substituted with one or two acidic substituents each independently selected from the group consisting of $—CO_2H$, $—SO_3H$, $—PO_3H_2$, $—OSO_3H$ and $—OPO_3H_2$. Values and alternative values for the remainder of the variables are as described above for Structural Formulas (I) or (Ia) or in the 1$^{st}$ specific embodiment, or first to third aspects thereof.

In a fifth aspect of the 1$^{st}$ specific embodiment of the present invention, R' is H and X is absent. Values and alternative values for the remainder of the variables are as described above for Structural Formulas (I) or (Ia) or in the 1$^{st}$ specific embodiment, or first to fourth aspects thereof.

In a sixth aspect of the 1$^{st}$ specific embodiment of the present invention, R is $(C_1-C_3)$alkyl substituted with one or two acidic substituents each independently selected from the group consisting of $—CO_2H$, $—SO_3H$, $—PO_3H_2$, $—OSO_3H$ and $—OPO_3H_2$. Values and alternative values for the remainder of the variables are as described above for Structural Formulas (I) or (Ia) or in the 1$^{st}$ specific embodiment, or first to fifth aspects thereof.

In a seventh aspect of the 1$^{st}$ specific embodiment of the present invention, R is $(C_6)$aryl$(C_1-C_3)$alkyl substituted with one or two acidic substituents each independently selected from the group consisting of $—CO_2H$, $—SO_3H$, $—PO_3H_2$, $—OSO_3H$ and $—OPO_3H_2$. Values and alternative values for the remainder of the variables are as described above for Structural Formulas (I) or (Ia) or in the 1$^{st}$ specific embodiment, or first to sixth aspects thereof.

In an eighth aspect of the 1$^{st}$ specific embodiment of the present invention, R is $(C_2)$alkyl substituted with one or two acidic substituents each independently selected from the group consisting of $—CO_2H$, $—SO_3H$, $—PO_3H_2$, $—OSO_3H$ and $—OPO_3H_2$. Values and alternative values for the remainder of the variables are as described above for Structural Formulas (I) or (Ia) or in the 1$^{st}$ specific embodiment, or first to seventh aspects thereof.

In a ninth aspect of the 1$^{st}$ specific embodiment of the present invention, R is $(C_6)$aryl substituted with one acidic substituent selected from the group consisting of $—CO_2H$, $—SO_3H$, $—PO_3H_2$, $—OSO_3H$ and $—OPO_3H_2$. Values and alternative values for the remainder of the variables are as described above for Structural Formulas (I) or (Ia) or in the 1$^{st}$ specific embodiment, or first to eighth aspects thereof.

In a tenth aspect of the 1$^{st}$ specific embodiment, the compound is represented by Structural Formula (I), wherein the values and alternative values are as described above for Structural Formulas (I) or (Ia) or in the 1$^{st}$ specific embodiment, or first to ninth aspects thereof.

In an eleventh aspect of the 1$^{st}$ specific embodiment, the compound is represented by Structural Formula (Ia), wherein the values and alternative values are as described above for Structural Formulas (I) or (Ia) or in the 1$^{st}$ specific embodiment, or first to tenth aspects thereof.

In a 2$^{nd}$ specific embodiment, the compound is represented by any one of the structural formulas in Table A, or a pharmaceutically acceptable salt or prodrug (e.g., a pharmaceutically acceptable salt) thereof.

TABLE A

| Cpd No. | Structural Formula |
|---|---|
| A | lipoyl-NH-CH₂CH₂-SO₃H |
| A' | (R)-lipoyl-NH-CH₂CH₂-SO₃H |
| B | lipoyl-N(CH₂CO₂H)₂ |
| B' | (R)-lipoyl-N(CH₂CO₂H)₂ |
| C | lipoyl-NH-CH(CO₂H)-CH₂CH₂-CO₂H |
| C' | (R)-lipoyl-L-Glu-OH |
| D | lipoyl-NH-CH(CH₂CH₂CO₂H)-C(O)-NH-CH₂-CO₂H |
| D' | (R)-lipoyl-L-Glu-Gly-OH |

TABLE A-continued

| Cpd No. | Structural Formula |
|---|---|
| E | lipoyl-Asp-Gly-OH |
| E' | (R)-lipoyl-L-Asp-Gly-OH |
| F | lipoyl-Gln-Gly-OH |
| F' | (R)-lipoyl-L-Gln-Gly-OH |
| G | lipoyl-Glu-Glu-OH |
| G' | (R)-lipoyl-L-Glu-L-Glu-OH |
| H | lipoyl-Glu-Ser-OH |
| H' | (R)-lipoyl-L-Glu-L-Ser-OH |

TABLE A-continued

| Cpd No. | Structural Formula |
|---|---|
| I | |
| I' | |
| J | |
| J' | |
| K | |
| K' | |
| L | |
| L' | |
| M | |
| M' | |
| N | |
| N' | |
| O | |
| O' | |
| Q | |
| Q' | |
| R | |
| R' | |

TABLE A-continued

| Cpd No. | Structural Formula |
|---|---|
| S | lipoyl-NH-CH(CO2H)-(CH2)3-CO2H (α-aminoadipic acid amide) |
| S' | lipoyl-(R)-NH-CH(CO2H)-(CH2)3-CO2H |
| T | lipoyl-NH-CH(CO2H)-CH2-CO2H (aspartic acid amide) |
| T' | lipoyl-(S)-NH-CH(CO2H)-CH2-CO2H |
| U | lipoyl-NH-CH2-CO2H (glycine amide) |
| U' | lipoyl-(R)-NH-CH2-CO2H |
| V | lipoyl-NH-CH(CH3)-CO2H (alanine amide) |
| V' | lipoyl-(R)-NH-C(S)(CH3)(H)-CO2H |
| W | lipoyl-NH-(CH2)3-CO2H |
| W' | lipoyl-(R)-NH-(CH2)3-CO2H |
| X | lipoyl-NH-CH(CO2H)-CH2-OPO3H2 (phosphoserine amide) |
| X' | lipoyl-(R)-NH-C(S)(CO2H)-CH2-OPO3H2 |
| Y | lipoyl-NH-CH(CO2H)-CH2F (fluoroalanine amide) |
| Y' | lipoyl-(R)-NH-C(S)(CO2H)-CH2F |
| Z | lipoyl-NH-CH(CO2H)-(CH2)2-CO2H (glutamic acid amide) |
| Z' | lipoyl-(R)-NH-C(S)(CO2H)-(CH2)2-CO2H |
| AB | lipoyl-NH-CH(CO2H)-CH2-C6H4-CO2H (carboxytyrosine-like) |
| AB' | lipoyl-(R)-NH-C(S)(CO2H)-CH2-C6H4-CO2H |
| AC | lipoyl-NH-C6H4-SO3H (meta-sulfonanilide) |

TABLE A-continued

| Cpd No. | Structural Formula |
|---|---|
| AC' | (structure) |
| AD | (structure) |
| AD' | (structure) |
| AE | (structure) |
| AE' | (structure) |
| AF | (structure) |
| AF' | (structure) |
| AG | (structure) |
| AG' | (structure) |
| AH | (structure) |
| AH' | (structure) |
| AI | (structure) |
| AI' | (structure) |

In a first aspect of the 2$^{nd}$ specific embodiment of the present invention, the (R)-lipoyl stereoisomer of any of the compounds in Table A is substantially separated from the (S)-lipoyl stereoisomer(s).

In a 3$^{rd}$ specific embodiment, the compound is represented by the following structural formula:

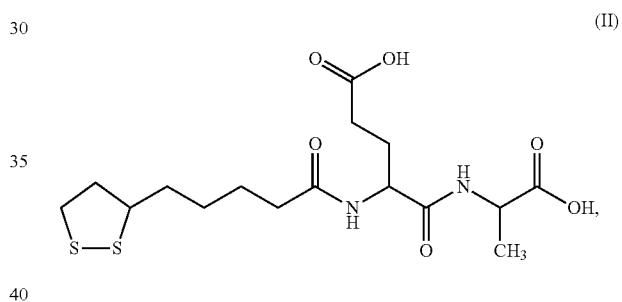

(II)

or a pharmaceutically acceptable salt thereof.

In a first aspect of the 3$^{rd}$ specific embodiment, the compound is represented by the following structural formula:

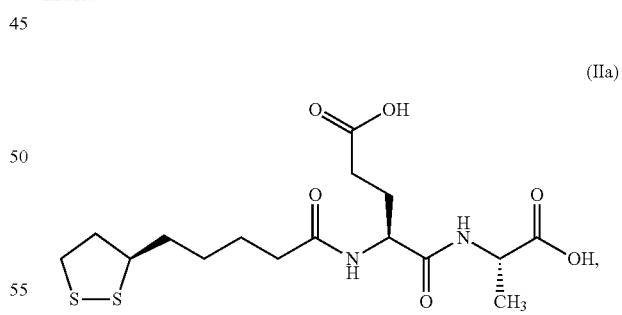

(IIa)

or a pharmaceutically acceptable salt thereof.

In a second aspect of the 3$^{rd}$ specific embodiment of the present invention, the (R)-lipoyl stereoisomer of the compound of Structural Formula II or IIa is substantially separated from the (S)-lipoyl stereoisomer(s).

The present invention relates, in one embodiment, to a method of treating and/or preventing the secondary cascade of neurodegenerative damage and/or improving long term functional outcomes associated with cognitive, behavior and sensorimotor function caused by a TBI, the method comprising administering (e.g., to a subject in need thereof) a compound (e.g., an effective amount of a compound) represented by Structural Formula (Ia), or a pharmaceutically acceptable salt or prodrug thereof.

The present invention relates, in another embodiment, to a method of treating and/or preventing the secondary cascade of neurodegenerative damage, and/or improving long term functional outcomes associated with cognitive, behavior and sensorimotor function caused by a TBI, the method comprising administering (e.g., to a subject in need thereof) a compound (e.g., an effective amount of a compound) represented by Structural Formula (I), wherein R is ($C_1$-$C_{18}$)alkyl, ($C_6$-$C_{18}$)aryl or ($C_6$-$C_{18}$)aryl($C_1$-$C_{18}$)alkyl and is substituted with at least one acidic substituent selected from the group consisting of —$CO_2H$, —$SO_3H$, —$PO_3H_2$, —$OSO_3H$, —$OPO_3H_2$, —$B(OH)_2$ and —NHOH, wherein the aryl of the ($C_6$-$C_{18}$)aryl or ($C_6$-$C_{18}$)aryl($C_1$-$C_{18}$)alkyl is optionally further substituted with one or more substituents selected from the group consisting of hydroxy, halo, ($C_1$-$C_3$)alkyl, halo($C_1$-$C_3$)alkyl, cyano, nitro, ($C_1$-$C_3$)alkoxy and thio($C_1$-$C_3$)alkyl.

In another embodiment, R is ($C_1$-$C_{18}$)alkyl. In another embodiment, R is ($C_1$-$C_3$)alkyl. In a further embodiment, R is ($C_3$)alkyl. In a further embodiment, R is ($C_2$)alkyl. Alternatively, R is ($C_1$)alkyl.

In another embodiment, R is ($C_6$-$C_{18}$)aryl. In a further embodiment, R is ($C_6$)aryl.

In another embodiment, R is ($C_6$-$C_{18}$)aryl($C_1$-$C_{18}$)alkyl. In a further embodiment, R is ($C_6$)aryl($C_1$-$C_3$)alkyl. Alternatively, R is ($C_6$)aryl($C_1$-$C_2$)alkyl.

In another embodiment, R is ($C_6$)aryl($C_2$)alkyl. In a further embodiment, R is ($C_6$)aryl($C_1$)alkyl.

In yet another embodiment, the at least one acidic substituent is selected from the group consisting of —$CO_2H$, —$SO_3H$, —$PO_3H_2$, —$OSO_3H$, —$OPO_3H_2$, —$B(OH)_2$ and —NHOH. In one embodiment, the at least one acidic substituent is selected from the group consisting of —$CO_2H$, —$SO_3H$, —$PO_3H_2$, —$OSO_3H$ and —$OPO_3H_2$.

In another embodiment, R is substituted with at least one acidic substituent selected from the group consisting of —$CO_2H$, —$SO_3H$, —$PO_3H_2$, —$OSO_3H$, —$OPO_3H_2$, —$B(OH)_2$ and —NHOH. In one embodiment, R is substituted with one, two or three acidic substituents. In a further embodiment, R is substituted with one or two acidic substituents.

In another embodiment, aryl is optionally further substituted with one or more substituents selected from the group consisting of hydroxy, halo, ($C_1$-$C_3$)alkyl, halo($C_1$-$C_3$)alkyl, cyano, nitro, ($C_1$-$C_3$)alkoxy and thio($C_1$-$C_3$)alkyl. In one embodiment, aryl is further substituted with one, two or three substituents. In another embodiment, aryl is substituted with one substituent. Alternatively, aryl is unsubstituted. In a further embodiment, aryl is further substituted with one or more substituents selected from the group consisting of hydroxyl and halo.

In another embodiment, R' is hydrogen or ($C_1$-$C_{18}$)alkyl, wherein said ($C_1$-$C_{18}$)alkyl is optionally substituted with one or more acidic substituents selected from the group consisting of —$CO_2H$, —$SO_3H$, —$PO_3H_2$, —$OSO_3H$, —$OPO_3H_2$, —$B(OH)_2$ and —NHOH. In one embodiment, R' is hydrogen.

In one embodiment, R' is ($C_1$-$C_{18}$)alkyl. In another embodiment, R' is ($C_1$-$C_3$)alkyl. In a further embodiment, R' is ($C_3$)alkyl. In a further embodiment, R' is ($C_2$)alkyl. Alternatively, R' is ($C_1$)alkyl.

In another embodiment, R' is substituted with at least one acidic substituent selected from the group consisting of —$CO_2H$, —$SO_3H$, —$PO_3H_2$, —$OSO_3H$, —$OPO_3H_2$, —$B(OH)_2$ and —NHOH. In one embodiment, R' is substituted with one, two or three acidic substituents. In another embodiment, R' is substituted with one or two acidic substituents. In a further embodiment, R' is substituted with one acidic substituent. Alternatively, R' is unsubstituted.

In another embodiment, X is absent or an amino acid, wherein the amino acid is oriented to form an amide linkage with —N(R')(R). For example, the moiety in N-lipoyl-glutamylalanine is oriented as shown in Structural Formula below:

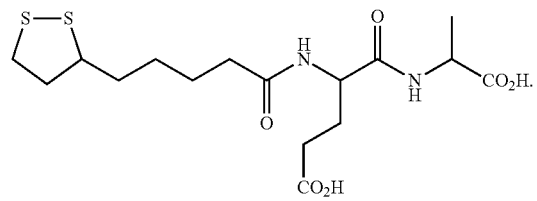 [SMILES: CC(NC(=O)C(CCC(=O)O)NC(=O)CCCCC1CCSS1)C(=O)O]

In one embodiment, X is absent. Alternatively, X is an amino acid. In a further embodiment, X is a naturally-occurring amino acid. In yet a further embodiment, X is aspartic acid, tyrosine, glutamic acid or alanine.

In a 4$^{th}$ specific embodiment, the method for treating or preventing secondary cascade of neurodegenerative damage and improving long term functional outcomes associated with cognitive, behavior and sensorimotor function caused by a TBI comprises administering an effective amount of compound represented by Structural Formula (I) or (Ia), or a pharmaceutically acceptable salt or prodrug thereof, wherein the values and alternative values for the variables are as described above.

In a first aspect of the 4$^{th}$ specific embodiment of the present invention, the (R)-lipoyl stereoisomer of a compound represented by Structural Formulas (I), or a pharmaceutically acceptable salt or prodrug thereof, is substantially separated from the (S)-lipoyl stereoisomer(s) or a pharmaceutically acceptable salt or prodrug thereof. Values and alternative values for the remainder of the variables are as described above for Structural Formula (I) or in the 4$^{th}$ specific embodiment.

In a second aspect of the 4$^{th}$ specific embodiment of the present invention, R' is H. Values and alternative values for the remainder of the variables are as described above for Structural Formulas (I) or in the 4$^{th}$ specific embodiment, or first aspect thereof.

In a third aspect of the 4$^{th}$ specific embodiment of the present invention, R' is H and X is a naturally-occurring amino acid. Values and alternative values for the remainder of the variables are as described above for Structural Formulas (I) or in the 4$^{th}$ specific embodiment, or first or second aspect thereof.

In a fourth aspect of the 4$^{th}$ specific embodiment of the present invention, R and R' are each ($C_1$-$C_3$)alkyl substituted with one or two acidic substituents each independently selected from —$CO_2H$, —$SO_3H$, —$PO_3H_2$, —$OSO_3H$ and —$OPO_3H_2$. Values and alternative values for the remainder of the variables are as described above for Structural Formula (I) or in the 4$^{th}$ specific embodiment, or first to third aspects thereof.

In a fifth aspect of the 4$^{th}$ specific embodiment of the present invention, R' is H and X is absent. Values and alternative values for the remainder of the variables are as described above for Structural Formulas (I) or in the 4th specific embodiment, or first to fourth aspects thereof.

In a sixth aspect of the 4th specific embodiment of the present invention, R is $(C_1-C_3)$alkyl substituted with one or two acidic substituents each independently selected from $-CO_2H$, $-SO_3H$, $-PO_3H_2$, $-OSO_3H$ and $-OPO_3H_2$. Values and alternative values for the remainder of the variables are as described above for Structural Formula (I) or in the 4th specific embodiment, or first to fifth aspects thereof.

In a seventh aspect of the 4th specific embodiment of the present invention, R is $(C_6)$aryl$(C_1-C_3)$alkyl substituted with one or two acidic substituents each independently selected from $-CO_2H$, $-SO_3H$, $-PO_3H_2$, $-OSO_3H$ and $-OPO_3H_2$. Values and alternative values for the remainder of the variables are as described above for Structural Formula (I) or in the 4th specific embodiment, or first to sixth aspects thereof.

In an eighth aspect of the 4th specific embodiment of the present invention, R is $(C_2)$alkyl substituted with one or two acidic substituents each independently selected from $-CO_2H$, $-SO_3H$, $-PO_3H_2$, $-OSO_3H$ and $-OPO_3H_2$. Values and alternative values for the remainder of the variables are as described above for Structural Formulas (I) or in the 4th specific embodiment, or first to seventh aspects thereof.

In a ninth aspect of the 4th specific embodiment of the present invention, R is $(C_6)$aryl substituted with one acidic substituent selected from $-CO_2H$, $-SO_3H$, $-PO_3H_2$, $-OSO_3H$ and $-OPO_3H_2$. Values and alternative values for the remainder of the variables are as described above for Structural Formulas (I) or in the 4th specific embodiment, or first to eighth aspects thereof.

In a tenth aspect of the 4th specific embodiment, the compound is represented by Structural Formula (I), wherein the values and alternative values are as described above for Structural Formulas (I) or in the 4th specific embodiment, or first to ninth aspects thereof.

In an eleventh aspect of the 4th specific embodiment, the compound is represented by Structural Formula (I), wherein the values and alternative values are as described above for Structural Formulas (I) or in the 4th specific embodiment, or first to tenth aspects thereof.

In a 5th specific embodiment, the method of this invention for treating or preventing the secondary cascade of neurodegenerative damage and improving long term functional outcomes associated with cognitive, behavior and sensorimotor function caused by a TBI comprises administering an effective amount of compound represented by one of the following structural formulas, or a pharmaceutically acceptable salt or prodrug thereof:

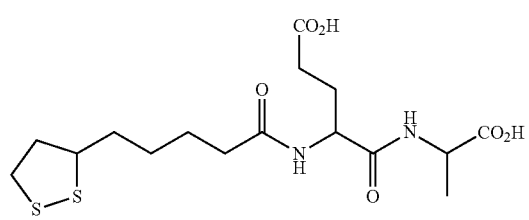
(CMX-2043)

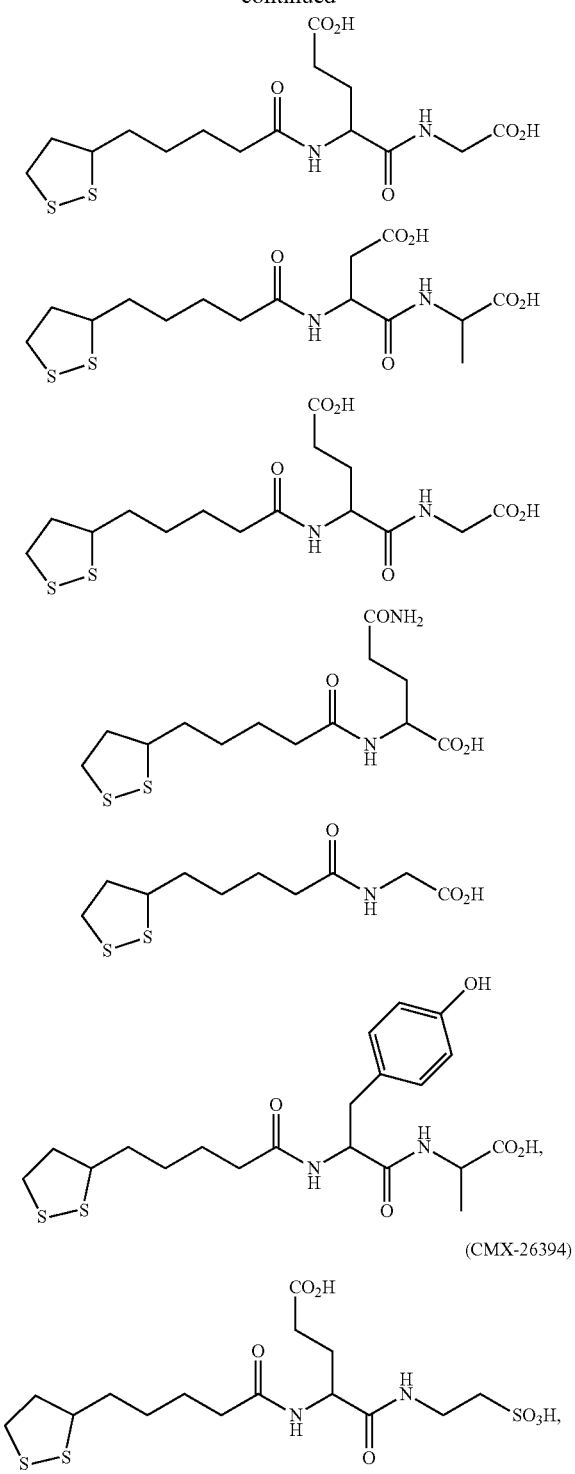
(CMX-26394)

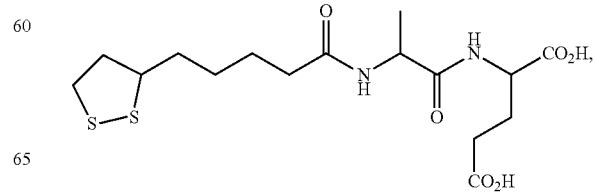

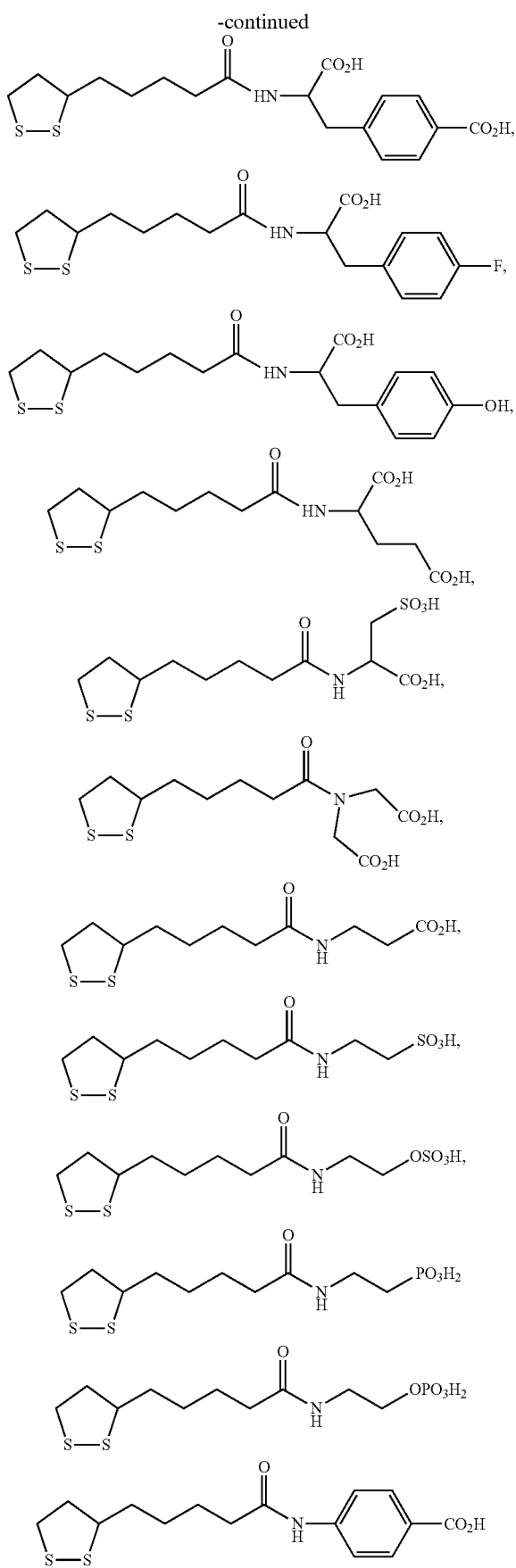

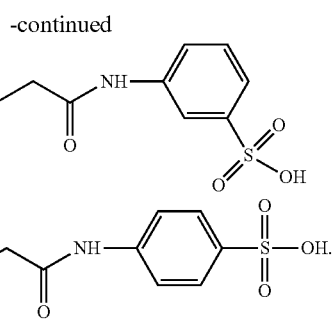

The invention also relates to pharmaceutically acceptable salts of the disclosed compounds of the present invention. The term "pharmaceutically acceptable salts" embraces salts commonly used to form alkali metal salts and to form addition salts of free bases. The nature of the salt is not critical, provided that it is pharmaceutically acceptable.

The pharmaceutically acceptable salts of the compounds of the present invention include base addition salts. Suitable pharmaceutically acceptable base addition salts of compounds of the present invention include, but are not limited to, metallic salts made from aluminum, calcium, lithium, magnesium, potassium, sodium and zinc or organic salts made from N,N'-dibenzylethylene-diamine, chloroprocaine, choline, diethanolamine, ethylenediamine, N-methylglucamine, lysine and procaine. All of these salts may be prepared by conventional means from a corresponding compound of the present invention by treating, for example, a compound described herein with the appropriate acid or base.

In one embodiment, the pharmaceutically acceptable salt comprises a monovalent or divalent cation. As used herein, "cation" refers to an atom or molecule that has a positive charge. A cation can be, for example, a metal or an amine. In a particular embodiment, the cation is a metal cation, such as a sodium cation.

As used herein, "amine salt" relates to a cation containing a protonated amino group. Amine salts include amino acid salts, such as lysine salts. In another embodiment, the cation is an amine and the pharmaceutically acceptable salt is an amine salt. In a particular embodiment, the pharmaceutically acceptable salt comprises lysine.

Salts can be chiral. When a disclosed salt has at least one chiral center and is named or depicted by structure without indicating the stereochemistry, it is to be understood that the name or structure encompasses one stereoisomer or enantiomer of the compound free from the corresponding stereoisomer(s) or enantiomer, a racemic mixture of the compound, or mixtures enriched in one stereoisomer or enantiomer relative to its corresponding stereoisomer(s) or enantiomer.

The invention also relates to pharmaceutically acceptable prodrugs of the disclosed compounds of the present invention.

In one embodiment, the invention relates to methods for treating and/or preventing TBI (e.g., the secondary cascade of neurodegenerative damage from a TBI, as by improving long term functional outcomes associated with cognitive, behavior and sensorimotor function), comprising administering an effective amount of a compound of Structural Formula (I) (e.g., to a subject in need thereof), wherein the hydrogen of each acidic functionality (e.g., —COOH, —SO$_3$H, —OSO$_3$H, —PO(OH)$_2$, —OPO(OH)$_2$) is optionally and independently replaced with a hydrolyzable group.

The invention also encompasses the use of pharmaceutically acceptable salts of the compounds including said hydrolyzable groups.

As used herein, the term "hydrolyzable group" refers to a moiety that, when present in a molecule of the invention, yields a carboxylic acid, or salt thereof, upon hydrolysis. Hydrolysis can occur, for example, spontaneously under acidic or basic conditions in a physiological environment (e.g., blood, metabolically active tissues, for example, liver, kidney, lung, brain), or can be catalyzed by an enzyme(s), (e.g., esterase, peptidases, hydrolases, oxidases, dehydrogenases, lyases or ligases). A hydrolyzable group can confer upon a compound of the invention advantageous properties in vivo, such as improved water solubility, improved circulating half-life in the blood, improved uptake, improved duration of action, or improved onset of action.

In one embodiment, the hydrolyzable group does not destroy the biological activity of the compound. In an alternative embodiment, a compound with a hydrolyzable group can be biologically inactive, but can be converted in vivo to a biologically active compound.

Compounds of the invention that include hydrolyzable groups may act as prodrugs. As used herein, the term "prodrug" means a compound that can be hydrolyzed, oxidized, metabolized or otherwise react under biological conditions to provide a compound of the invention. Prodrugs may become active upon such reaction under biological conditions, or they may have activity in their unreacted forms. A prodrug may undergo reduced metabolism under physiological conditions (e.g., due to the presence of a hydrolyzable group), thereby resulting in improved circulating half-life of the prodrug (e.g., in the blood). Prodrugs can typically be prepared using well-known methods, such as those described by Burger's Medicinal Chemistry and Drug Discovery (1995) 172-178, 949-982 (Manfred E. Wolff ed., 50 Ed).

In one embodiment, the hydrolyzable group is selected from the group consisting of $(C_1-C_{10})$alkyl, $(C_2-C_{10})$alkenyl, $(C_2-C_{10})$alkynyl, $(C_1-C_{10})$alkoxy$(C_1-C_{10})$alkyl, $(C_1-C_{10})$alkoxy$(C_1-C_{10})$alkoxy$(C_1-C_{10})$alkyl, aryl and aryl$(C_1-C_{10})$alkyl, wherein each is optionally substituted with 1 to 3 substituents selected from the group consisting of halo, nitro, cyano, cyclopropyl, cyclobutyl, cyclopentyl, cyclohexyl, amino, $(C_1-C_6)$alkylamino, di$(C_1-C_6)$alkylamino, $(C_1-C_6)$alkyl, halo$(C_1-C_6)$alkyl, $(C_1-C_6)$alkoxy, halo$(C_1-C_6)$alkoxy, morpholino, phenyl, and benzyl.

In another embodiment, the hydrolyzable group is selected from the group consisting of methyl, ethyl, n-propyl, isopropyl, n-butyl, sec-butyl, isobutyl, tert-butyl, pentyl, hexyl, heptyl, allyl, ethoxymethyl, methoxyethyl, methoxyethoxymethyl, methoxyethoxyethyl, benzyl, pentafluorophenyl, 2-N-(morpoholino)ethyl, dimethylaminoethyl and para-methoxybenzyl.

Certain methods of this invention are useful for improving long term functional outcomes associated with cognitive, behavior and sensorimotor function. Improvements in such functional outcomes can be assessed using cognitive, behavior and sensorimotor tests that are within the ordinary skill of the art.

The methods of this invention also comprise administering a compound of Structural Formula (I) in a pharmaceutical composition. Thus, provided herein are methods for treating and/or preventing (e.g., treating) TBI in a subject in need thereof, comprising administering to the subject a pharmaceutical composition comprising a pharmaceutically acceptable carrier or diluent and an effective amount of a compound of Structural Formula (I), or a pharmaceutically acceptable salt or prodrug thereof. The pharmaceutical compositions disclosed herein are prepared in accordance with standard procedures and are administered at dosages that are selected to reduce, prevent, eliminate, or to slow or halt the progression of, the condition being treated. See, e.g., *Remington's Pharmaceutical Sciences*, 17th ed., Remington, J. P., Easton, Pa., Mack Publishing Company, 2005, and *Goodman and Gilman's The Pharmaceutical Basis of Therapeutics*, 12th ed., Brunton, L. et. als., eds., New York, McGraw-Hill, 2010, the contents of which are incorporated herein by reference, for a general description of the methods for administering various agents for human therapy. The pharmaceutical compositions can be delivered using controlled or sustained-release delivery systems (e.g., capsules, bioerodable matrices). Exemplary delayed-release delivery systems for drug delivery that would be suitable for administration of the pharmaceutical compositions are described in U.S. Pat. No. 5,990,092 (issued to Walsh); U.S. Pat. No. 5,039,660 (issued to Leonard); U.S. Pat. No. 4,452,775 (issued to Kent); and U.S. Pat. No. 3,854,480 (issued to Zaffaroni).

The compositions of the present invention comprise one or more compounds of Structural Formulas (I) and/or (Ia), or a pharmaceutically acceptable salt or prodrug thereof, in association with one or more nontoxic, pharmaceutically acceptable carriers and/or diluents and/or adjuvants and/or excipients, collectively referred to herein as "carrier" materials, and optionally, other active ingredients. The compositions may contain from about 0.01% to about 99% by weight of the active ingredient, depending on the method of administration.

For preparing compositions from the compounds of the present invention, pharmaceutically acceptable carriers can either be solid or liquid. Solid form preparations include powders, tablets, pills, capsules, cachets, suppositories, and dispersible granules. For example, the compounds of the present invention may be in powder form for reconstitution at the time of delivery. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is in a mixture with the finely divided active ingredient.

In tablets, the active ingredient is mixed with the carrier having the necessary binding properties in suitable proportions and compacted in the shape and size desired.

The powders and tablets preferably contain from about one to about seventy percent of the active ingredient. Suitable carriers are magnesium carbonate, magnesium stearate, talc, sugar, lactose, pectin, dextrin, starch, gelatin, tragacanth, methylcellulose, sodium caboxymethylcellulose, a low-melting wax, cocoa butter, and the like. Tablets, powders, cachets, lozenges, fast-melt strips, capsules and pills can be used as solid dosage forms containing the active ingredient suitable for oral administration.

Liquid form preparations include solutions, suspensions, retention enemas, and emulsions, for example, water or water propylene glycol solutions. For parenteral injection, liquid preparations can be formulated in solution in aqueous polyethylene glycol.

Aqueous solutions suitable for oral administration can be prepared by dissolving the active ingredient in water and adding suitable colorants, flavors, stabilizing agents, and thickening agents as desired. Aqueous suspensions for oral administration can be prepared by dispersing the finely divided active ingredient in water with viscous material, such as natural or synthetic gums, resins, methylcellulose, sodium carboxymethylcellulose, and other well-known suspending agents.

Alternatively, the compounds or compositions of the present invention can be in powder form for reconstitution at the time of delivery.

The composition is preferably in unit dosage form. In such form, the composition is subdivided into unit doses containing appropriate quantities of the active ingredient. The unit dosage form can be a packaged preparation, the package containing discrete quantities of, for example, tablets, powders, and capsules in vials or ampules. Also, the unit dosage form can be a tablet, cachet, capsule, or lozenge itself, or it can be the appropriate amount of any of these in packaged form. The quantity of active ingredient in a unit dose preparation may be varied or adjusted from about 0.1 mg to about 1000 mg, preferably from about 0.1 mg to about 100 mg (e.g., for intravenous administration) or from about 1.0 mg to about 1000 mg (e.g., for oral administration). The dosages, however, may be varied depending upon the requirements of the subject, the severity of the condition being treated, the compound and the route of administration being employed. Determination of the proper dosage for a particular situation is within the skill in the art. In one embodiment, the dosage is from about 0.01 mg/kg to about 100 mg/kg.

In general, the methods for delivering the disclosed compounds and pharmaceutical compositions of the invention in vivo utilize art-recognized protocols for delivering the agent with the only substantial procedural modification being the substitution of the compounds represented by any one of the disclosed compounds for the drugs in the art-recognized protocols.

The pharmaceutical compositions useful in the methods of the present invention may be administered by a variety of routes or modes, which include, but are not limited to, parenteral, oral, intratracheal, sublingual, pulmonary, topical, rectal, nasal, buccal, vaginal, or via an implanted reservoir. Implanted reservoirs may function by mechanical, osmotic, or other means. The compounds and compositions may also be administered intravascularly, intramuscularly, subcutaneously, intraperitoneally, intracardiacally, orally or topically. The term "parenteral", as understood and used herein, includes intravenous, intracranial, intraperitoneal, paravertebral, periarticular, periostal, subcutaneous, intracutaneous, intra-arterial, intramuscular, intra articular, intrasynovial, intrasternal, intrathecal, and intralesional injection or infusion techniques. Such compositions are preferably formulated for parenteral administration, and most preferably for intravenous, intracranial, or intra-arterial administration. Generally, and particularly when administration is intravenous or intra-arterial, pharmaceutical compositions may be given as a bolus, as two or more doses separated in time, or as a constant or non-linear flow infusion.

Methods of making compounds of Structural Formula I, as well as details of their biological activities, are disclosed, for example, in International Publication No. WO 2010/132657 and International Publication No. WO 2012/067947, the relevant teachings of which are incorporated by reference herein in their entirety.

The synthesis and preparation of the lipoyl compounds useful in the methods of the invention are also described in U.S. Pat. Nos. 9,540,417 and 9,359,325, which are incorporated herein by reference in their entireties. The methods for synthesizing and purifying the lipoyl compounds of the invention are also described in Kates, S. A., Casale, R. A., Baguisi, A., Beeuwkes, R. Bioorganic and Medicinal Chemistry, 2014, 22, 505-512, which methods are hereby incorporated by reference in their entirety.

Pharmaceutical compositions comprising compounds of Structural Formula I and methods for preparing pharmaceutical compositions comprising compounds of Structural Formula I are disclosed, for example, in International Publication No. WO 2015/174948, the relevant teachings of which are incorporated by reference herein in their entirety.

Pharmaceutical compositions useful in the methods of this invention can be administered to a subject, such as a mammal, particularly a human, in a manner similar to other therapeutic, prophylactic, and diagnostic agents, and especially compositions comprising therapeutic hormone peptides. The dosage to be administered, and the mode of administration will depend on a variety of factors including age, weight, sex, condition of the subject, and genetic factors, and will ultimately be decided by the attending physician or veterinarian. In general, the dosage required for diagnostic sensitivity or therapeutic efficacy will range from about 0.001 to 1000.0 mg/kg of host body mass (also referred to herein as body weight).

Pharmaceutically acceptable salts of the lipoyl compounds useful in this invention include, for example, those derived from pharmaceutically acceptable inorganic and organic acids and bases. Examples of suitable acids include hydrochloric, hydrobromic, sulfuric, nitric, perchloric, fumaric, maleic, malic, pamoic, phosphoric, glycolic, lactic, salicylic, succinic, toluene-p-sulfonic, tartaric, acetic, citric, methanesulfonic, formic, benzoic, malonic, naphthalene-2-sulfonic, tannic, carboxymethyl cellulose, polylactic, polyglycolic, and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and $N-(C_{1-4}\text{ alkyl})_{4+}$ salts.

It should be understood that the lipoyl compounds useful in the methods of this invention may be modified to enhance certain biological properties, in particular the ability to treat or prevent secondary brain damage caused by TBI. Such modifications are known in the art and include those which increase the ability of the lipoyl compound to penetrate or be transported into a given biological system (e.g., circulatory system, lymphatic system), increase oral availability, increase solubility to allow administration by injection, alter the metabolism of the lipoyl compound, and alter the rate of excretion of the lipoyl compound. In addition, lipoyl compounds may be altered to a pro-drug form such that the desired lipoyl compound is created in the body of an individual as the result of the action of metabolic or other biochemical processes on the pro-drug. Such pro-drug forms typically demonstrate little or no activity in in vitro assays. Some examples of pro-drug forms may include ketal, acetal, oxime, and hydrazone forms of compounds, which contain ketone or aldehyde groups. Other examples of pro-drug forms include the hemi-ketal, hemi-acetal, acyloxy ketal, acyloxy acetal, ketal, and acetal forms.

Pharmaceutically acceptable carriers, adjuvants and vehicles that may be used in the pharmaceutical compositions useful in the methods of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene polyoxypropylene block polymers, polyethylene glycol and wool fat.

The pharmaceutical compositions used in the methods of this invention may be in the form of a sterile, injectable preparation, for example, a sterile, injectable aqueous or oleaginous suspension. Such a suspension may be formulated according to techniques known in the art using suitable dispersing or wetting agents (such as, for example, Tween 80) and suspending agents. The sterile injectable preparation may also be a sterile, injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspension medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long chain alcohol diluent or dispersant such as those described in *Pharmacoplia Halselica*.

The pharmaceutical compositions useful in the methods of this invention may be administered in any orally acceptable dosage form, including, but not limited to, aqueous solutions and suspensions, capsules, tablets, caplets, pills, oleaginous suspensions and solutions, syrups, and elixirs. In the case of tablets for oral use, carriers, which are commonly used include lactose and cornstarch. Lubricating agents, such as magnesium stearate, are also typically added. For oral administration in a capsule form, useful diluents include lactose and dried cornstarch. Capsules, tablets, pills, and caplets may be formulated for delayed or sustained release.

For oral administration, the compositions may also be in the form of, for example, a tablet, capsule, suspension or liquid. The composition is preferably made in the form of a dosage unit containing an effective amount of the active ingredient. Examples of such dosage units are tablets and capsules. For therapeutic purposes, the tablets and capsules can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica, or talc; disintegrants, for example potato starch, flavoring or coloring agents, or acceptable wetting agents. Oral liquid preparations generally in the form of aqueous or oily solutions, suspensions, emulsions, syrups or elixirs may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

When aqueous suspensions are to be administered orally, other emulsifying and/or suspending agents may be added to the pharmaceutical compositions used in the methods of the present invention. If desired, certain sweetening and/or flavoring and/or coloring agents may be added. Formulations for oral administration may contain 10%-95% (weight/volume, w/v) active ingredient, and preferably 25%-70% (w/v). Preferably, a pharmaceutical composition for oral administration prevents or inhibits hydrolysis of the lipoyl compound by the digestive system, but allows absorption into the blood stream.

The compositions may also be administered parenterally via, for example, injection. Formulations for parenteral administration can be in the form of aqueous or non-aqueous isotonic sterile injection solutions or suspensions. These solutions or suspensions can be prepared from sterile powders or granules having one or more of the carriers mentioned for use in the formulations for oral administration. The compounds can be dissolved in polyethylene glycol, propylene glycol, ethanol, corn oil, benzyl alcohol, sodium chloride, and/or various buffers.

Delivery can also be by injection into the brain or body cavity of a patient or by use of a timed release or sustained release matrix delivery systems, or by onsite delivery using micelles, gels and liposomes. Nebulizing devices, powder inhalers, and aerosolized solutions are representative of methods that may be used to administer such preparations to the respiratory tract. Delivery can be in vitro, in vivo, or ex vivo.

For certain methods of this invention, the pharmaceutical compositions may also be administered in the form of suppositories for vaginal or rectal administration. These compositions can be prepared by mixing a lipoyl compound described herein with a suitable non-irritating excipient, which is solid at room temperature, but liquid at body temperature, so that the composition will melt in a relevant body space to release the active ingredient. Such materials include, but are not limited to, cocoa butter, beeswax and polyethylene glycols. Formulations for administration by suppository may contain 0.5%-10% (w/v) active ingredient, preferably 1%-2% (w/v).

Topical administration of the pharmaceutical compositions used in the methods of the invention may also be useful. For application topically, a suitable ointment carrier may be added. Carriers for topical administration include, but are not limited to, mineral oil, liquid petroleum, white petroleum, propylene glycol, polyoxyethylene polyoxypropylene compound, emulsifying wax and water. Alternatively, a suitable lotion or cream carrier may be used. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of the present invention may also be formulated for topical or other application as a jelly, gel, or emollient, where appropriate. The pharmaceutical compositions may also be topically applied to the lower intestinal tract by rectal suppository formulation or in a suitable enema formulation. Topical administration may also be accomplished via transdermal patches.

For topical use, the compounds disclosed herein may also be prepared in suitable forms to be applied to the skin, or mucus membranes of the nose and throat, and may take the form of creams, ointments, liquid sprays or inhalants, lozenges, or throat paints. Such topical formulations further can include chemical compounds such as dimethylsulfoxide (DMSO) to facilitate surface penetration of the active ingredient. Suitable carriers for topical administration include oil-in-water or water-in-oil emulsions using mineral oils, petrolatum and the like, as well as gels such as hydrogel. Alternative topical formulations include shampoo preparations, oral pastes and mouthwash.

For application to the eyes or ears, the compounds of the present invention may be presented in liquid or semi-liquid form formulated in hydrophobic or hydrophilic bases as ointments, creams, lotions, paints or powders.

The pharmaceutical compositions useful in the methods of the present invention may also be administered by inhalation through the nose or mouth, in which case absorption may occur via the mucus membranes of the nose or mouth, or inhalation into the lungs. Such modes of administration typically require a composition to be provided in the form of a powder, solution, or liquid suspension, which is then mixed with a gas (e.g., air, oxygen, nitrogen, or combinations thereof) so as to generate an aerosol or suspension of droplets or particles. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. In a preferred embodiment, pharmaceutical compositions of the present invention are administered to a subject by inhalation.

In certain embodiments of the methods of the present invention, the lipoyl compound is selectively delivered to the brain. For the purposes of the present invention, "selective delivery to the brain" or "selectively delivered to the brain" is intended to mean that the agent is administered directly to the brain of the subject (e.g., by a shunt or catheter; see, e.g., U.S. Patent Application Publication No. US 2008/0051691), to the perispinal space of the subject without direct intrathecal injection (see, e.g., U.S. Pat. No. 7,214,658), or in a form which facilitates delivery across the blood brain barrier thereby reducing potential side effects in other organs or tissues. In this regard, formulation of the lipoyl compound into a nanoparticle made by polymerization of a monomer (e.g., a methylmethacrylate, polylactic acid, polylactic acid-polyglycolic acid-copolymer, or polyglutaraldehyde) in the presence of a stabilizer allows for passage through the blood brain barrier without affecting other organs with the agent. See, e.g., U.S. Pat. No. 7,402,573, incorporated herein by reference in its entirety.

In one embodiment of the present invention, the lipoyl compound is delivered to the brain via an exosome, in particular an exosome modified with a moiety that targets cells of the brain. Exosomes suitable for use in this invention can be prepared by conventional methods, see, e.g., Sun, et al. (2010) Mol. Ther. 18:1606-1614. Likewise, compounds can be encapsulated within exosomes by conventional methods, e.g., incubating the compound with an exosome preparation in saline at room temperature for several minutes, and separating the exosomes from unencapsulated compound and debris, e.g., by sucrose gradient separation. As described in the relevant art, moieties that target cells of the brain include peptides that target cells of the brain (e.g., neurons, microglia and/or oligodendrocytes) as well as other targeting agents such as lipopolysaccharide, which has a high affinity for surface markers on microglia (Chow, et al. (1999) J. Biol. Chem. 274:10689-10692). Targeting peptides include, e.g., RVG peptides, which may be fused to membrane bound proteins, e.g., Lamp2b (lysosome-associated membrane protein 2b) to facilitate integration into the exosome. Untargeted or brain-targeted liposome has also been used successfully to facilitate delivery of small molecule inhibitors to brain tissue (Pardridge, W. M. 2007. Adv. Drug Deliv. Rev. 59:141-152; Pulford et al. 2010. PLoS ONE 5:e11085). As a result, embodiments of the methods of the present invention include use of liposomes that are either targeted or untargeted.

The pharmaceutical compositions useful in the methods of the present invention may also be formulated as slow release formulations. Such formulations may be administered by implantation, for example, subcutaneously or intramuscularly or by intramuscular injection. Such formulations may be prepared according to techniques well known in the art of pharmaceutical formulation, for example, as an emulsion in an acceptable oil, or ion exchange resins, or as sparingly soluble derivatives (e.g. sparingly soluble salts).

The pharmaceutical compositions useful in the methods of the present invention may be packaged in a variety of ways appropriate to the dosage form and mode of administration. These include but are not limited to vials, bottles, cans, packets, ampoules, cartons, flexible containers, inhalers, and nebulizers. Such compositions may be packaged for single or multiple administrations from the same container. Kits, of one or more doses, may be provided containing the composition in dry powder or lyophilized form and an appropriate diluent, which are to be combined shortly before administration; and instructions for preparation and/or administration of the reconstituted or otherwise prepared pharmaceutical composition. The pharmaceutical compositions may also be packaged in single use pre-filled syringes, or in cartridges for auto-injectors and needleless jet injectors.

Multi-use packaging may require the addition of antimicrobial agents such as phenol, benzyl alcohol, meta-cresol, methyl paraben, propyl paraben, benzalconium chloride, and benzethonium chloride, at concentrations that will prevent the growth of bacteria, fungi, and the like, but are non-toxic when administered to a patient.

Details concerning dosages, dosage forms, modes of administration, composition can be found in a standard pharmaceutical text, such as Remington's Pharmaceutical Sciences (1990), which is incorporated herein by reference.

The dosages of a compound disclosed herein to a subject may be varied depending upon the requirements of the subject, the severity of the condition being treated, the route of administration and the compound being employed. Determination of the proper dosage for a particular situation is within the skill in the art. For example, suitable dosages for administration to humans can be extrapolated from data obtained in experiments performed on animal (e.g., rat) models. Guidance for extrapolating non-human animal model dosage data to human dosages can be found, for example, in *FDA Draft Guidance: Estimating the Safe Starting Dose in Clinical Trials for Therapeutics in Adult Healthy Volunteers* (2005).

For example, suitable intravenous dosages of a compound of the invention can be from about 0.001 mg/kg to about 100 mg/kg, from about 0.01 mg/kg to about 100 mg/kg, from about 0.01 mg/kg to about 10 mg/kg, from about 0.01 mg/kg to about 1 mg/kg body weight per treatment. Determining the dosage and route of administration for a particular agent, subject and TBI is well within the abilities of one of skill in the art. Preferably, the dosage does not cause or produces minimal adverse side effects.

An effective amount of a compound of the invention can be administered alone, or in combination with, one or more other therapeutic agents in the methods disclosed herein.

Thus, a compound of the invention can be administered as part of a combination therapy (e.g., with one or more other therapeutic agents). The compound of the invention can be administered before, after or concurrently with one or more other therapeutic agents. In some embodiments, a compound of the invention and other therapeutic agent can be co-administered simultaneously (e.g., concurrently) as either separate formulations or as a joint formulation. Alternatively, the agents can be administered sequentially, as separate compositions, within an appropriate time frame, as determined by the skilled clinician (e.g., a time sufficient to allow an overlap of the pharmaceutical effects of the therapies). A lipoyl compound and one or more other therapeutic agents can be administered in a single dose or in multiple doses, in an order and on a schedule suitable to achieve a desired therapeutic effect (e.g., a reduction in and/or inhibition of joint inflammation; a reduction in and/or inhibition of ischemia, a reduction in and/or inhibition of an ischemic injury; a reduction in and/or inhibition of an ischemia-reperfusion injury). Suitable dosages and regimens of administration can be determined by a clinician and are dependent on the agent(s) chosen, pharmaceutical formulation and route of administration, various patient factors and other considerations.

The present invention is described in the following Examples, which are set forth to aid in the understanding of the invention, and should not be construed to limit in any way the scope of the invention as defined in the claims which follow thereafter.

EXAMPLES

Example 1: Efficacy of CMX-2043 in a Fluid Percussion Model of Diffused Traumatic Brain Injury (TBI) in Rats Procedures On the day before TBI surgery (Day −1), rats were anesthetized with 3% isoflurane in a mixture of nitrous oxide and oxygen (2:1) for induction of anesthesia and then maintained at 1-3% isoflurane in a mixture of nitrous oxide and oxygen (2:1). The surgical site skin was shaved, and the rat was then placed in a stereotaxic frame. Buprenorphine SR, s.c, (0.9-1.2 mg/kg Zoopharm: Lot: BSR1-142111) and Cefazolin, i.p., (40-50 mg/kg; Hospira: Lot: 101D032) was given at this time. The skull was exposed through a midline incision. A parasagittal craniotomy (5 mm) using a trephine drill was performed at 1 mm posterior to bregma and 1 mm lateral to the midline (outer circumference). A sterile plastic injury tube (the plastic connector hub of a sterile needle cut 1 cm in length and trimmed to fill the craniotomy securely) was placed over the exposed dura and bonded by super glue to the skull. Dental cement was then poured around the injury tube to obtain a complete seal. After the dental cement had hardened, the injury tube was filled with sterile saline and the skin was closed by surgical clips. The animals were then returned to a clean home cage after recovery from the anesthesia.

On the day of TBI surgery (Day 0), rats were re-anesthetized with 3% isoflurane in a mixture of nitrous oxide and oxygen (2:1), intubated, connected to a respirator and ventilated with 1-2% isoflurane in a mixture of nitrous oxide and oxygen (2:1). Cefazolin (40-50 mg/kg) was given again at this time. The surgical site was opened to expose the injury tube. The seal and connection were checked, and the injury tube was refilled with sterile saline. The rats were then connected to the fluid percussion (F-P) device. The (F-P) device consists of a plexiglass cylindrical reservoir bounded at one end by a rubber-covered plexiglass piston with the opposite end fitted with a transducer housing and a central injury connector adapted for the rat's skull. The entire system was filled with sterilized distilled water at room temperature. The (aseptic) metal injury connector was next firmly connected to the plastic injury tube of the intubated and anesthetized rat. The injury was induced by the descent of a metal pendulum striking the piston, thereby injecting a small volume of fluid (sterile saline followed by small amount of sterilized distilled water) into the closed cranial cavity and producing a brief displacement of neural tissue. The amplitude of the resulting pressure pulse was measured in atmospheres by a pressure transducer. A moderate (2.5-3.0 atmospheres) injury was induced. The injury tube was removed and skin was then closed by surgical clips. The animals were returned to their home cage after extubation and recovery from the anesthesia.

Dosing Solution and Dosing

Dosing solutions were prepared in a blinded fashion with H, I, M, O and Z labels ready to use. Animals received intravenous injections of H, I, M, O or Z at 30 minutes after TBI and again at 24 hours after TBI. After all the data were collected and presented, the solutions were uncoded into the groups: H=Vehicle, I=CMX 2043 30 mg/kg, M=CMX 2043 15 mg/kg, O=CMX 2043 45 mg/kg and Z=CMX 2043 7.5 mg/kg.

Behavioral Tests

Functional activities were evaluated using:

1. Limb placing tests. These tests were performed prior to surgery (Day pre), one (Day 1), three (Day 3), seven (Day 7), fourteen (Day 14), twenty-one (Day 21) and twenty-eight (Day 28) days after TBI. (Day 0=day of TBI.)

Limb placing tests were divided into both forelimb and hindlimb tests. For the forelimb-placing test, the examiner held the rat close to a tabletop and scored the rat's ability to place the forelimb on the tabletop in response to whisker, visual, tactile, or proprioceptive stimulation. For the hindlimb placing test, the examiner assessed the rat's ability to place the hindlimb on the tabletop in response to tactile and proprioceptive stimulation. Separate sub-scores were obtained for each mode of sensory input (half-point designations possible), and added to give total scores (for the forelimb placing test: 0=normal, 12=maximally impaired; for the hindlimb placing test: 0=normal; 6=maximally impaired). A total limb placing score was calculated as ½(total left forelimb score)+total left hindlimb score.

2. Body swing test. These tests were performed twenty-one (Day 21, Day 22 for animals #3 to #14) and twenty-eight (Day 28) days after TBI. (Day 0=day of TBI.)

The rat was held approximately one inch from the base of its tail. It was then elevated to an inch above a surface of a table. The rat was held in the vertical axis, defined as no more than 100 to either the left or the right side. A swing was recorded whenever the rat moved its head out of the vertical axis to either side. The rat must have returned to the vertical position for the next swing to be counted. Thirty (30) total swings were counted. A normal rat typically has an equal number of swings to either side. Following focal ischemia, the rat tends to swing to the contralateral (left) side. The test was performed at the same times as the limb placing tests.

Sacrifice and Brain Collection

At twenty-eight (28) days after TBI (after the behavioral tests), animals were anesthetized deeply with ketamine/xylazine (50-100 mg/kg ketamine, 5-10 mg/kg xylazine, i.p.). The animals were then perfused transcardially with normal saline (with heparin 2 unit/ml) followed by 10% formalin. Brains were removed and stored in 10% formalin.

Data Analysis:

All data were expressed as mean S.E.M. Behavioral data and weight were analyzed by repeated measures of ANOVA and/or ANCOVA. For the limb placing tests, the day before TBI (Day pre) was not included in the analysis to ensure normal distribution of the data.

Behavioral Tests

Limb placing test (see FIG. 1): Animals receiving CMX 2043 15 mg/kg, 30 mg/kg and 45 mg/kg showed superior recovery compared to vehicle-treated animals ($p<0.001$) starting 1 day following TBI.

Figure 2:
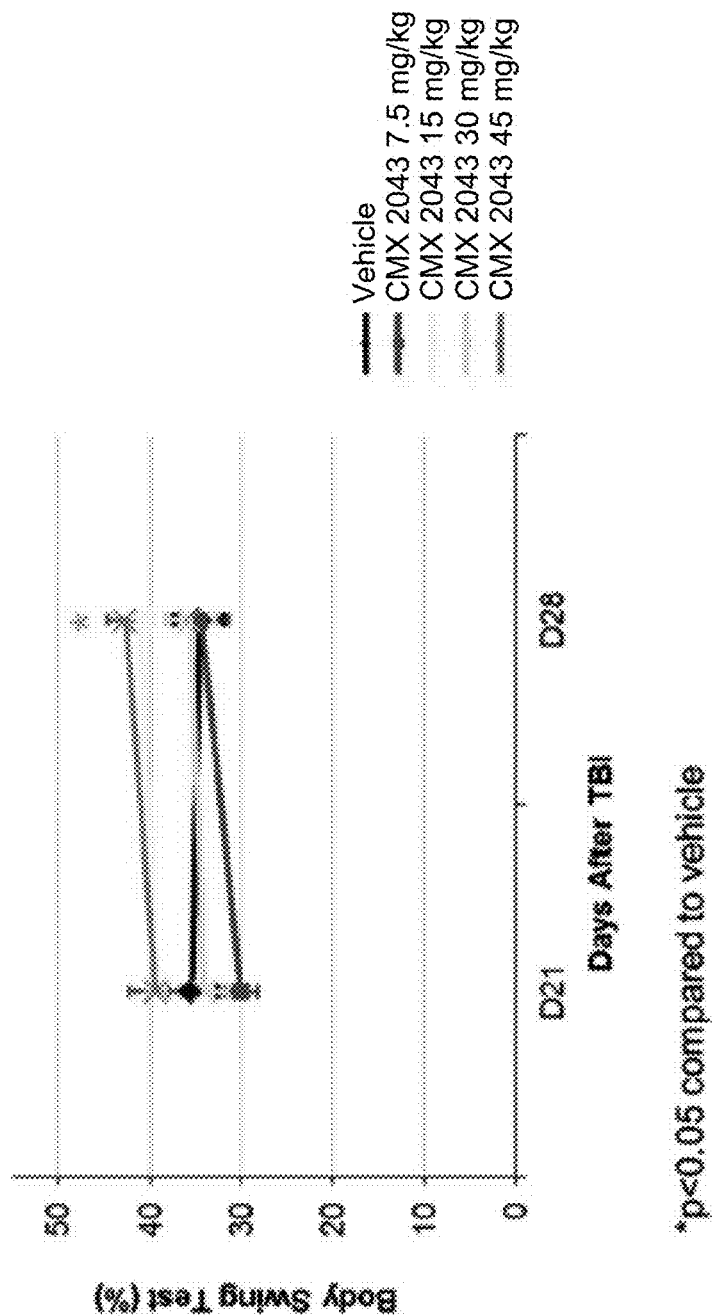
FIG. 2 shows the results of a body swing test in rats following treatment with different doses of CMX-2043 in a fluid percussion model of diffused TBI. *P<0.05 indicates a significant difference from saline treated animals.

Body swing test (see FIG. 2): Animals receiving CMX 2043 45 mg/kg showed superior recovery compared to vehicle-treated animals ($p<0.05$) on Day 28.

Figure 3:
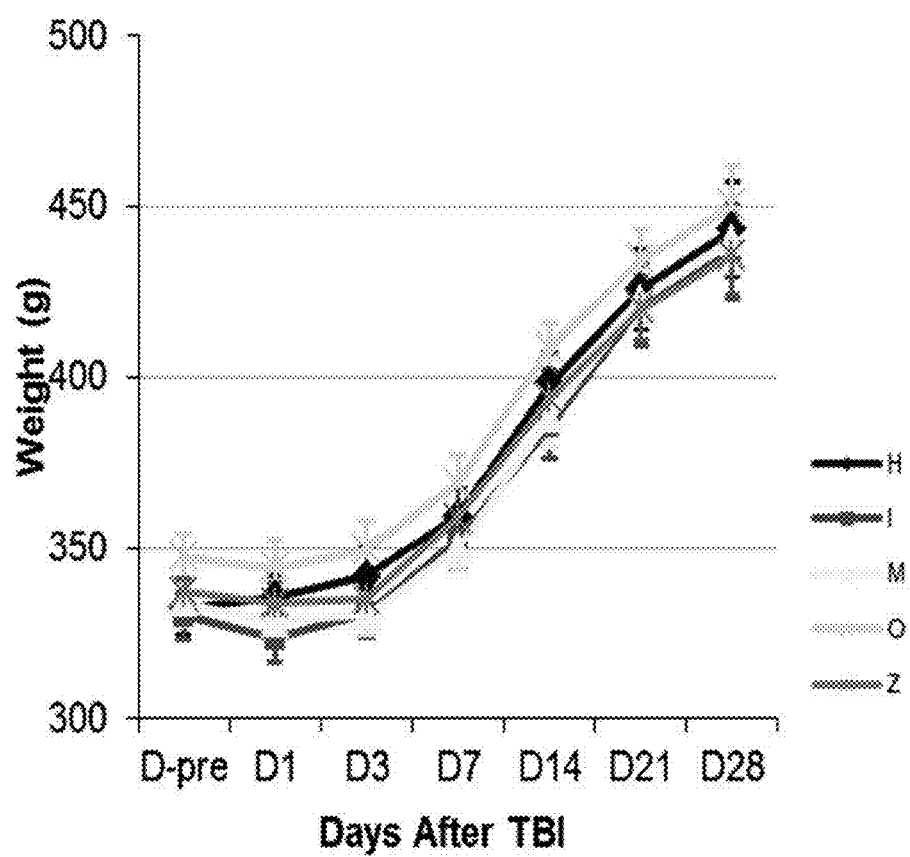
FIG. 3 shows the body weight change in rats following treatment with different doses of CMX-2043 in a fluid percussion model of diffused TBI. H=Vehicle, I=CMX 2043 30 mg/kg, M=CMX 2043 15 mg/kg, O=CMX 2043 45 mg/kg and Z=CMX 2043 7.5 mg/kg.

Weight changes (see FIG. 3): There were no significant differences among CMX 2043 and vehicle treated groups in body weight over time.

Conclusions

TBI was made in mature male Sprague-Dawley rats, resulting in focal unilateral cerebral contusion. CMX 2043 7.5 mg/kg, 15 mg/kg, 30 mg/kg or 45 mg/kg was given intravenously starting 30 minutes after TBI, and repeated at 24 hours after TBI. Behavioral assessments of sensorimotor function, including limb placing tests were made prior to TBI and 1 day, 3 days, 7 days, 14 days, 21 days and 28 days after TBI. The body swing test was performed 21 (or 22) days and 28 days after TBI.

This blinded, randomized study showed significant enhancement of sensorimotor performance in limb placing test with CMX 2043 (15 mg/kg, 30 mg/kg and 45 mg/kg each dosing); and in body swing test with CMX 45 mg/kg starting 30 minutes after TBI. These results suggest that CMX 2043 may be potentially useful in improving sensorimotor recovery after TBI at doses 15 mg/kg, 30 mg/kg and 45 mg/kg.

Example 2: Evaluation of Efficacy of CMX-2043 and CMX-26394 in the Morris Water Maze Tests in a Rat Model of Focal TBI Animals Adult, male, Spague-Dawley rats from Charles River were used. Animals were received at PsychoGenics and assigned unique identification numbers (tails marked). Animals were housed 2 per cage in polycarbonate rat cages equipped with microisolators and acclimated for up to 7 days. All rats were examined, handled, and weighed prior to initiation of the study to assure adequate health and suitability. During the course of the study, 12/12 light/dark cycles were maintained. The room temperature was maintained between 20 and 23° C. with a relative humidity maintained around 50%. Chow and water were provided ad libitum for the duration of the study. Animals were randomly assigned across treatment groups.

Bilateral Controlled Cortical Impact (BCCI) Traumatic Brain Injury (TBI)

BCCI TBI to the medial frontal cortex (MFC) was induced by a cortical contusion device (Custom Design & Fabrication, Inc [CDF], Richmond, Va.). This device creates a reliable contusion injury to the exposed area of the brain with a brass-tipped impounder. (Hoffman et al., 1994). Rats were anesthetized with isoflurane (5%) (Novaplus™), and 02 (300 $cm^3$/min), and mounted in a stereotaxic frame. Under aseptic conditions, a sagittal incision was made in the scalp and the fascia retracted to expose the cranium. Then, a 6-mm diameter trephine drill was used to open the skull immediately anterior to the bregma. TBI of the MFC was made with a 5-mm-diameter rounded brass impactor attached to a computer-controlled piston propelled electronically with following parameters: velocity=2.5 m/s; depth=3 mm; duration=100 ms). After BCCI, any cortical surface hemorrhaging was controlled and the fascia and scalp sutured. The animals were allowed to recover in a warmed recovery chamber and appropriate post-operative care was taken.

Treatment Groups

Treatment was delivered 30 minutes after injury and at approximately 24 hrs after injury.

TABLE 1

Treatment Groups

| Group | N | Treatment |
|---|---|---|
| 1 | 10 | TBI + Saline 1 mL/kg IV |
| 2 | 10 | TBI + CMX-2043 30 mg/kg IV |
|  | 20 | Total Animals |

Beam Balance

The beam balance test examined vestibulomotor reflex activity of the animals after injury. Animals were trained prior to surgery to maintain their balance on the beam for up to 60 sec. The rats were tested during the first week after injury (D3, D5, D7). The animal was gently placed on a suspended narrow beam 1.5 cm wide with a rough surface and the duration for which it remained on the beam was measured with a maximum cutoff time of 60 sec. Each animals received three trials per test day and the trials where averaged to obtain a beam balance time. Cushioned pads were placed on the floor to prevent injury in the event the animals fell.

Morris Water Maze

Two weeks after injury, rats were tested in the Morris water maze (MWM). The MWM is a well-characterized test of spatial learning and memory in rodents. The objective of the MWM is to teach rats that there is an escape platform located somewhere in a large, water filled pool. The rats are naturally motivated to escape the pool. The rats use extra-maze visual cues to locate the position of a submerged platform over a series of trials.

Figure 4A:
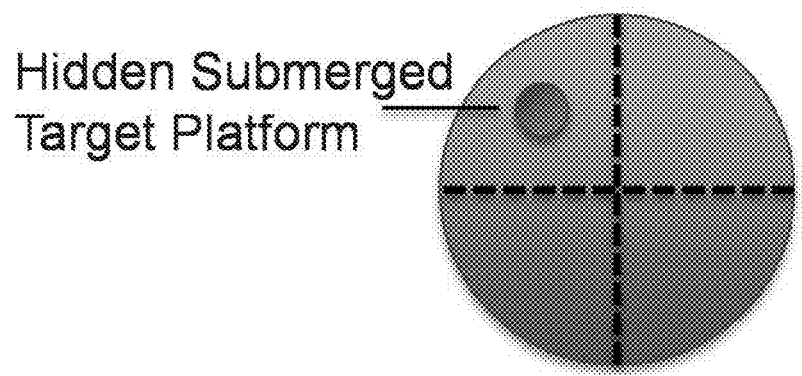
FIGS. 4A and 4B are schematic illustrations of a Morris water maze pool.

The MWM test was conducted beginning at day 14 after traumatic brain injury. Rats were acclimated to the test room at least 1 hour prior to testing. The MWM consists of a circular pool (160 cm diameter×50 cm height) containing water that was made opaque with non-toxic black paint in order to hide the escape platform (see FIG. 4A). The water temperature was kept at 25±1° C. The water surface was 15 cm from the rim of the pool, and the inner wall was always carefully wiped to eliminate any local cues. The pool was located in a large room with a number of extra-maze visual cues, including highly visible geometric images (squares, triangles, circles, etc.) hung on the wall, diffuse lighting, and curtains to hide the experimenter and the awaiting rats. Behavior was tracked by a video camera hanging above the pool. Video tracking software (ANY-maze) recorded and analyzed the behavior of the animal in the pool. After training, the rats were gently dried with clean paper towels and placed in a warmed holding cage for the rats to dry before being returned to their home cage.

Training: During training, the rat was placed into the water facing the wall of the pool and allowed to search for the platform. If the rat found the platform within 60 seconds, the trial was stopped, and the rat was allowed to stay on the platform for 30 seconds before being moved. If the platform was not found within 60 seconds, rats were placed on the platform for 30 sec in order to allow them time to learn the position of the platform in relation of the room's visual cues. Rats were given 4 trials a day for 4 days (days 14 to 17), with a 30 second interval between trials. The starting point was randomly rotated for every rat in each trial.

Figure 4B:
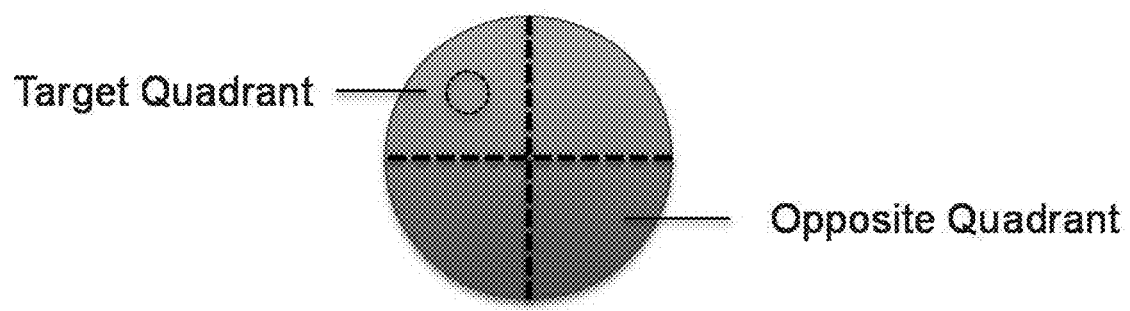

Probe Trial: On the fifth day (day 18 after surgery), the rats received a probe trial. The probe test consisted of placing the animal in the pool for 60 seconds without the platform and monitoring the time spent in the four quadrants of the pool (see FIG. 4B). An animal that has learned the position of the platform will spend more time searching that target quadrant of the pool. During training, a submerged hidden target platform is placed in the pool and this region is defined as the target quadrant (see FIG. 4A). During the probe trial, the platform is removed and the duration of swimming in the different quadrants is tracked by the video camera and computer. The number of entries into the zone previously occupied by the target platform is also tracked.

Statistical Analysis

Data are presented as mean±SEM and analyzed by one-way repeated measures Analysis of variance (ANOVA) in order to test the effects of treatment on beam balance times and Morris water maze performance. Significant main effects were followed by post hoc comparisons. An effect was considered significant if $p<0.05$.

Results

Figure 5:
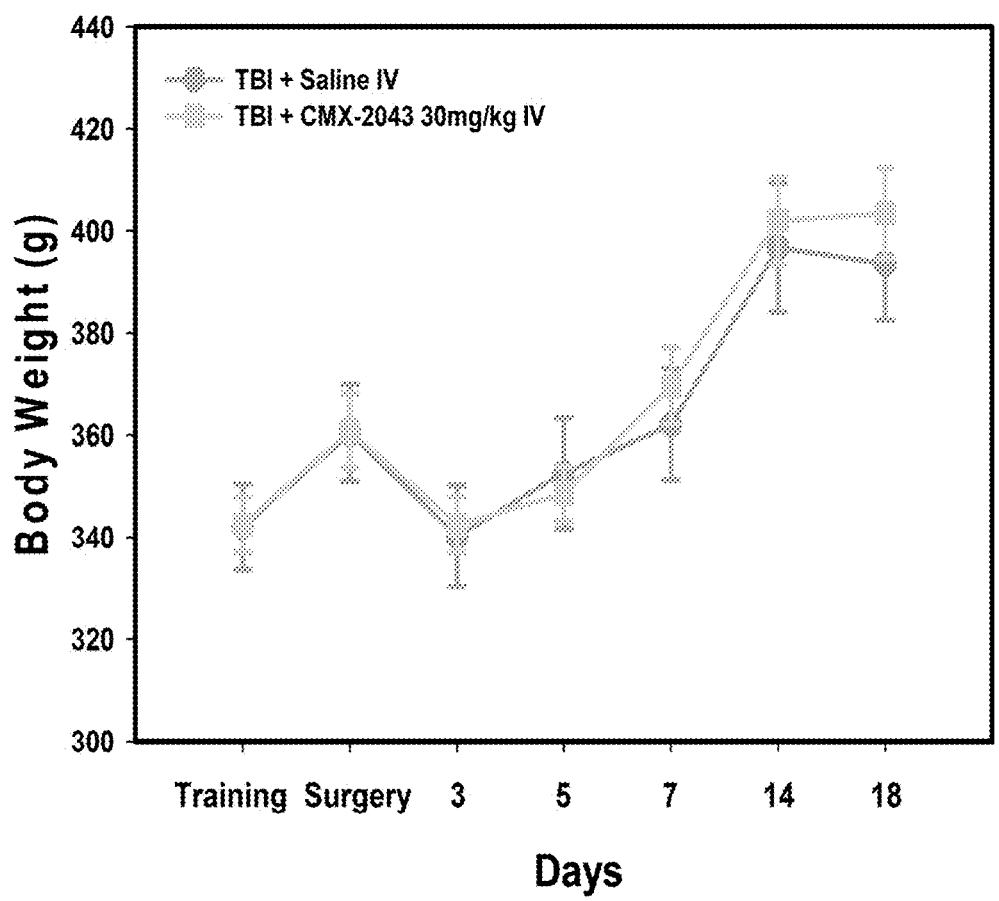
FIG. 5 shows the effect of treatment with CMX-2043 on body weights of rats in a focal model of traumatic brain injury. Data are presented as mean±SEM. n=10 Saline; n=9 CMX-2043.

Body Weight and Post-Operative Observations: The effects of treatment with CMX-2043 on body weights are shown in FIG. 5. The weight of the animals declined immediately after surgery, but began to recover by days 3 and 5. There was no significant difference in body weights between any of the treatment groups, indicating that treatment with CMX-2043 had no adverse effects on weight gain during the study.

One animal in the first CMX-2043 group died within 24 hours post-injury. An extra contingency replacement animal was added to this group during the second surgical cohort. In this second cohort, another animal in the CMX-2043 group also died within 24 hours post-injury leaving 9 surviving animals of the 11 animals treated in this group.

Figure 6:
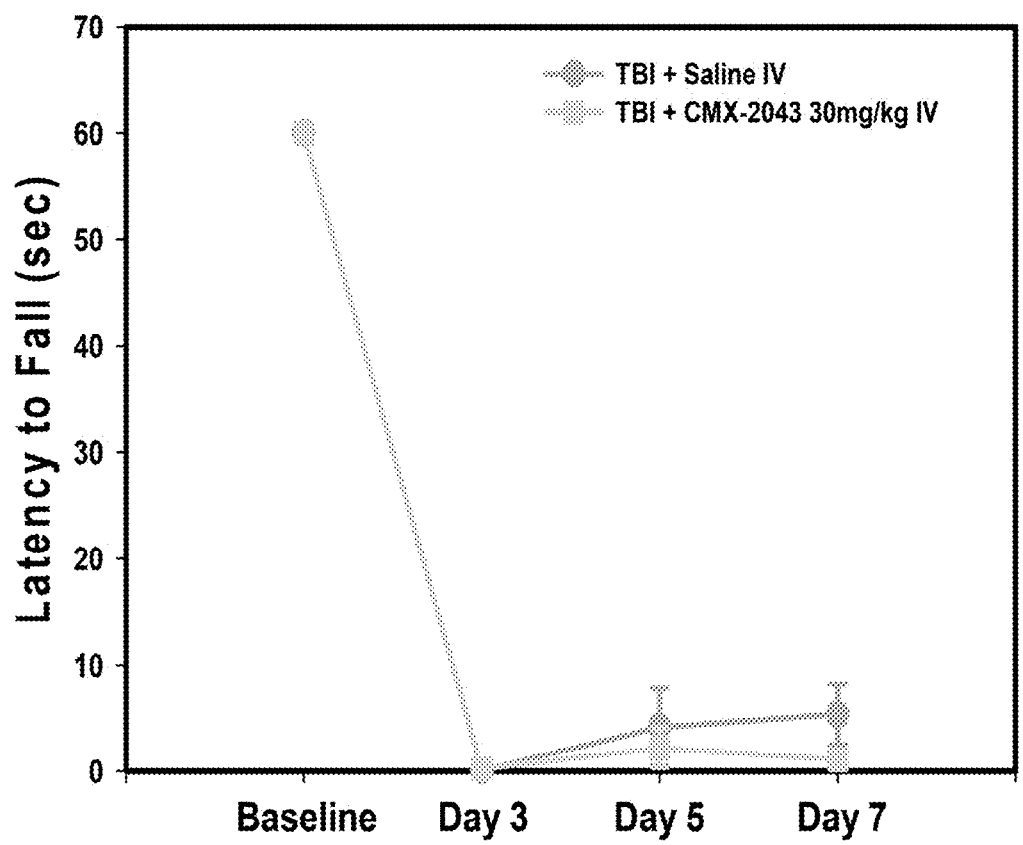
FIG. 6 shows the effect of TBI treatment with CMX-2043 on beam balance times. Data are presented as mean±SEM. n=10 Saline; n=9 CMX-2043.

Beam balance: The effects of TBI treatment with CMX-2043 on the beam balance following injury are shown in FIG. 6. Prior to injury, all animals were able to maintain their balance on the beam for at least 60 seconds. At Day 3 following injury, beam balance times were reduced to less than 3 seconds in all groups.

Figure 7:
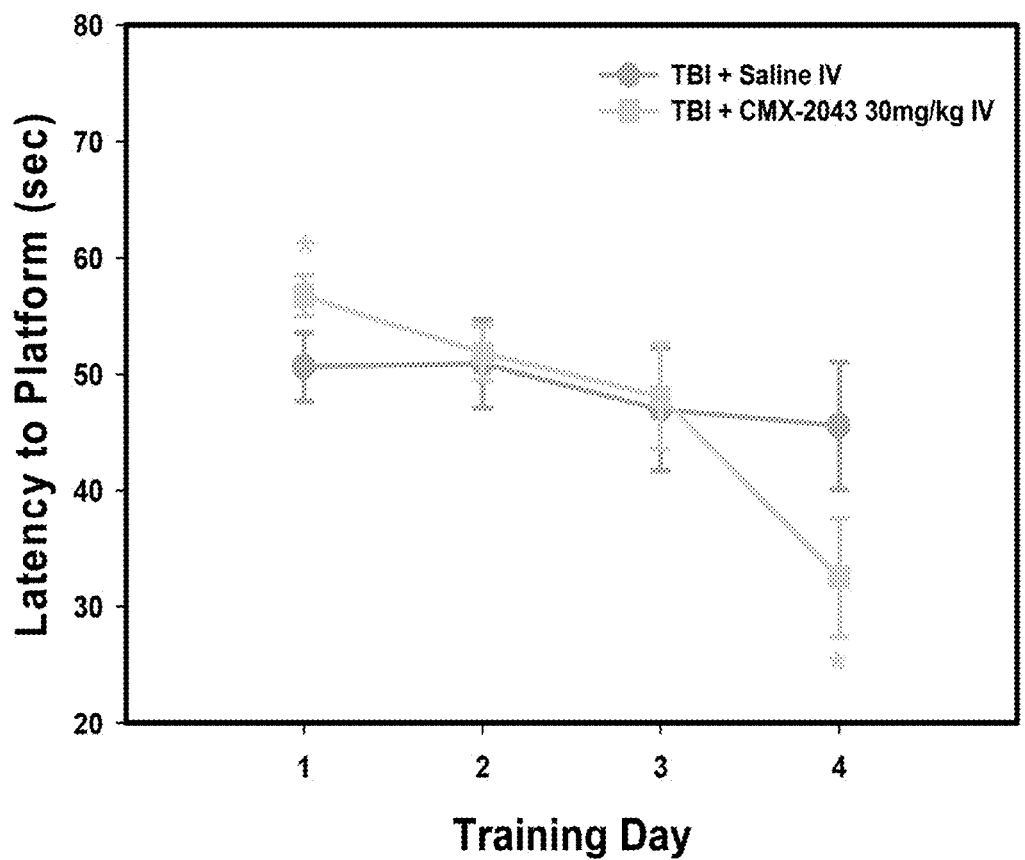
FIG. 7 shows the effect of treatment with CMX-2043 on escape latency from a Morris water maze. Data represent mean±SEM. n=10 Saline; n=9 CMX-2043. *P<0.05 indicates a significant difference from saline treated animals.

Morris water maze escape latency: The effects of TBI treatment with CMX-2043 on MWM escape latency in TBI-injured rats are shown in FIG. 7.

On days 14 through 17 following injury, animals were trained to locate the escape platform in the Morris water maze. A shorter escape latency period indicates improved learning and memory of the platform's location.

Repeated-measures ANOVA detected a significant difference between groups. Post hoc comparisons showed that on day 1 of training, animals treated with 30 mg/kg CMX-2043 exhibited longer latency times than saline treated animals. There were no differences between groups on training days 2 and 3. On the final training day, TBI animals treated with 30 mg/kg CMX-2043 exhibited a significantly faster escape latency than animals treated with saline.

Figure 8:
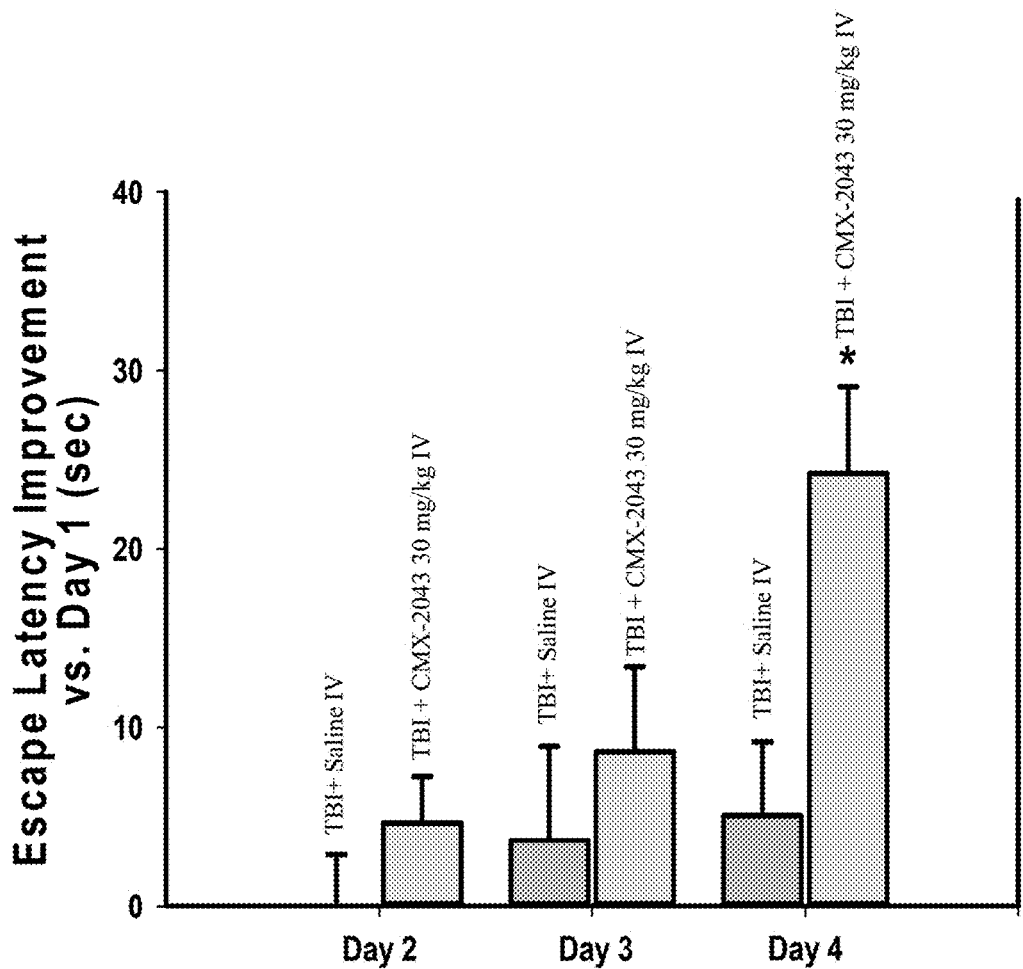
FIG. 8 shows the effect of TBI treatment with CMX-2043 on the improvement in escape latency from a Morris water maze. Data represent mean±SEM. n=10 Saline; n=9 CMX-2043. *P<0.05 indicates a significant difference from saline treated animals.

Morris water maze improvement in escape latency: In an alternative analysis of the MWM escape latency data, the improvement in the escape latency was calculated relative to each individual animal's Day 1 performance. The effects of treatment with CMX-2043 or CMX-26394 on escape latency improvement are shown in FIG. 8. Saline treated animals did not show any improvement in escape latency at Day 2 and showed only a modest 5 sec improvement by Day 4 of training. In contrast, animals treated with 30 mg/kg CMX-2043 showed steady improvement in escape latency at Day 2 (4.9 sec), Day 3 (8.7 sec), and Day 4 (24.2 sec) where the improvement was significantly better than for saline controls. Animals treated with 15 mg/kg also exhibited progressive improvement in escape latency at Day 3 (6.8 sec) and Day 4 (15.0 sec; $p=0.07$ compared to saline treatment).

Figure 9:
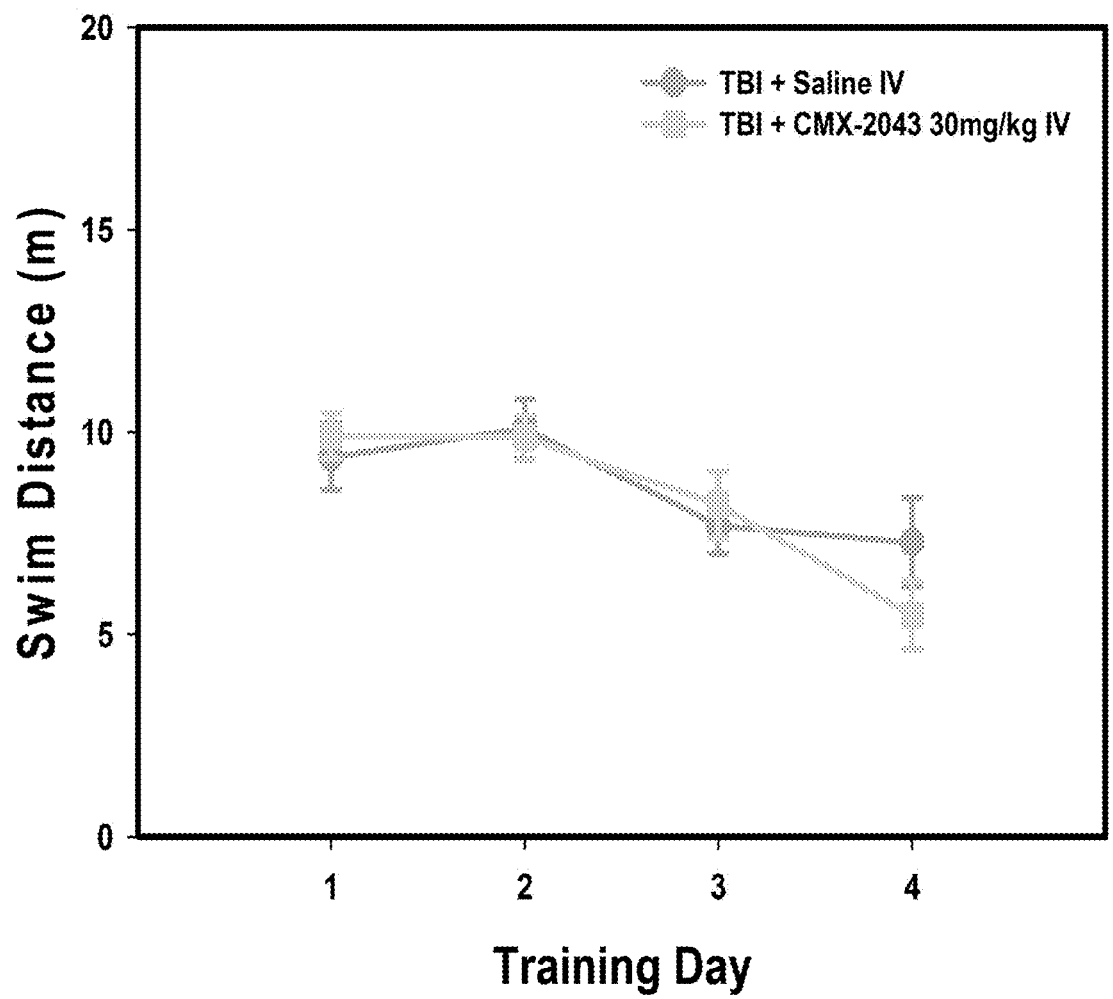
FIG. 9 shows the effect of TBI treatment with CMX-2043 on swim distance during Morris water maze training. Data represent mean±SEM. n=10 Saline; n=9 CMX-2043.
Figure 10:
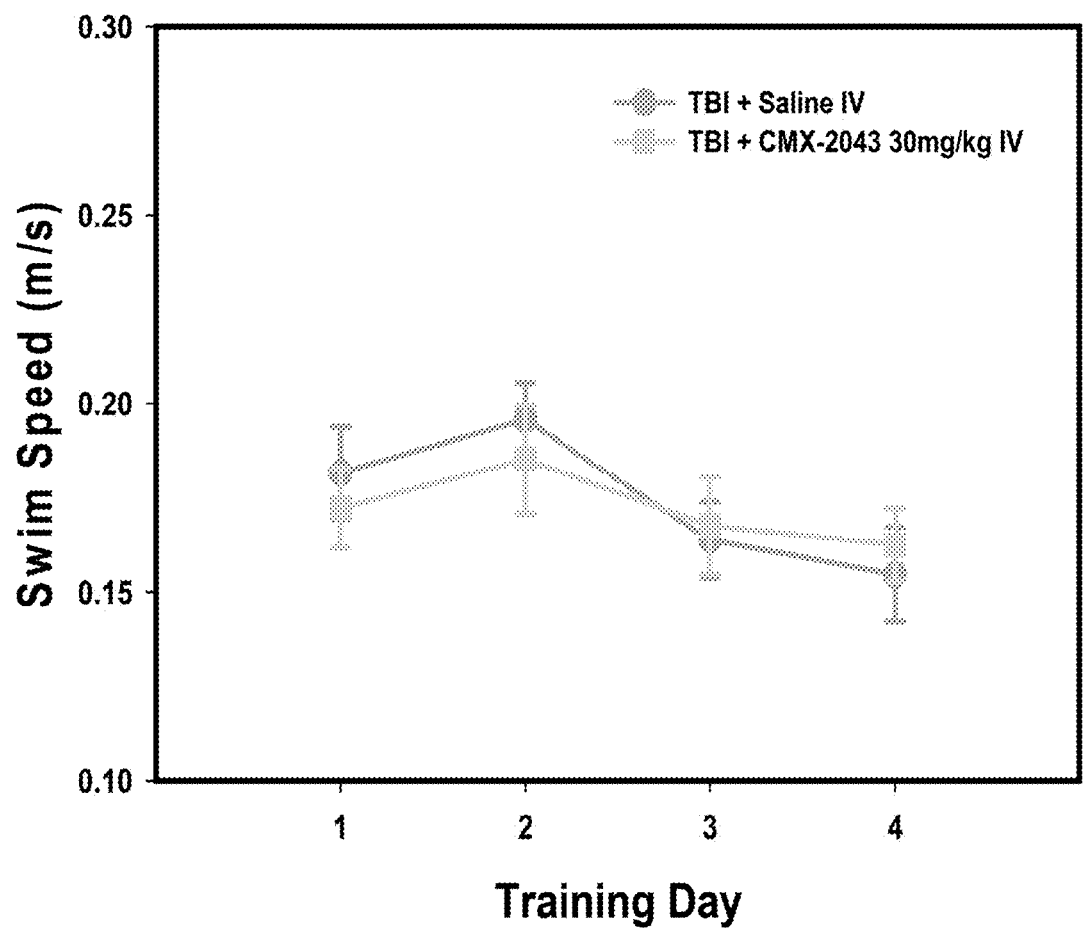
FIG. 10 shows the effect of TBI treatment with CMX-2043 on swim speed during Morris water maze training. Data represent mean±SEM. n=10 Saline; n=9 CMX-2043.

Morris water maze swim distance and swim speed: The effects of TBI treatment with CMX-2043 on MWM swim distance and swim speed in TBI-injured rats are shown in FIGS. 9 and 10.

In addition to the escape latency, the Morris water maze test also yields the swim distance and swim speed of the animals while they search for the escape platform.

Repeated-measures ANOVA showed no difference in both swim distance and the swim speed between treatment groups. These results indicate that the improved escape latency observed in animals treated with 30 mg/kg CMX-2043 is attributable to cognitive improvements rather than differences in motor ability during swimming.

Figure 11:
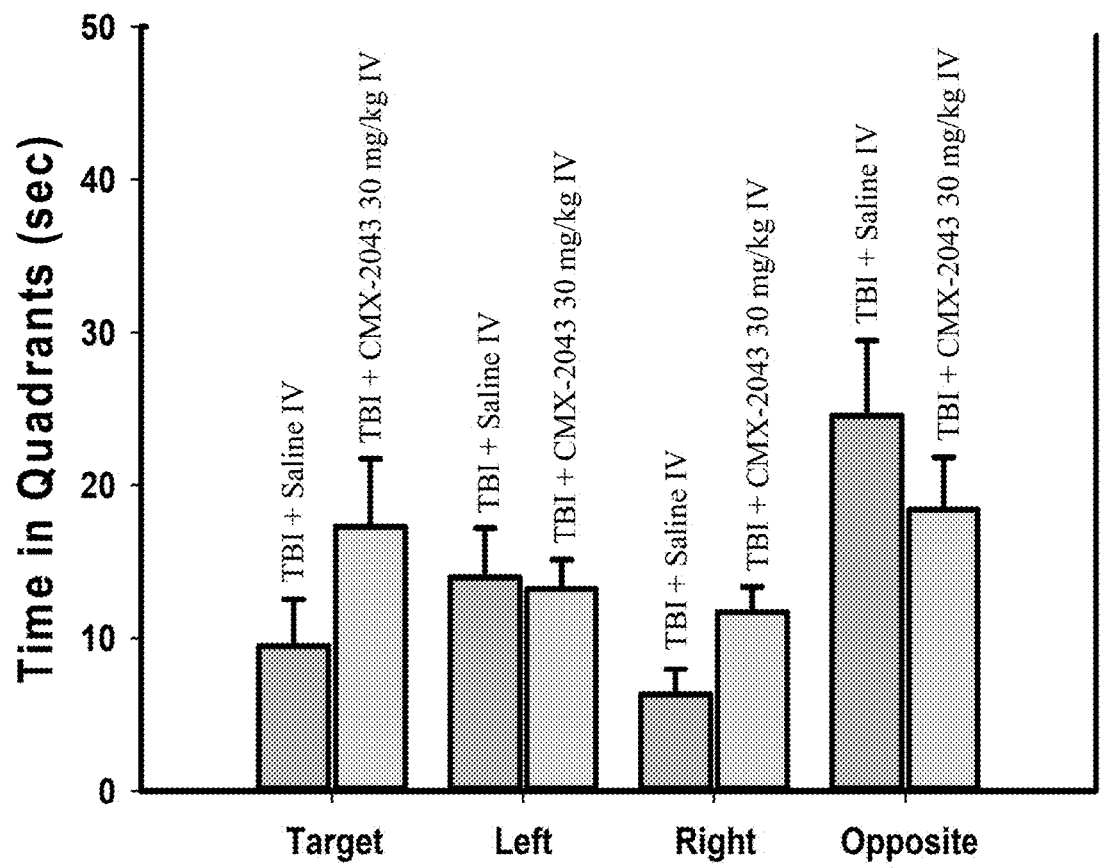
FIG. 11 shows the effect of TBI treatment with CMX-2043 on time spent in each quadrant during Morris water maze probe trial. Data represent mean±SEM. n=10 Saline; n=9 CMX-2043.
Figure 12:
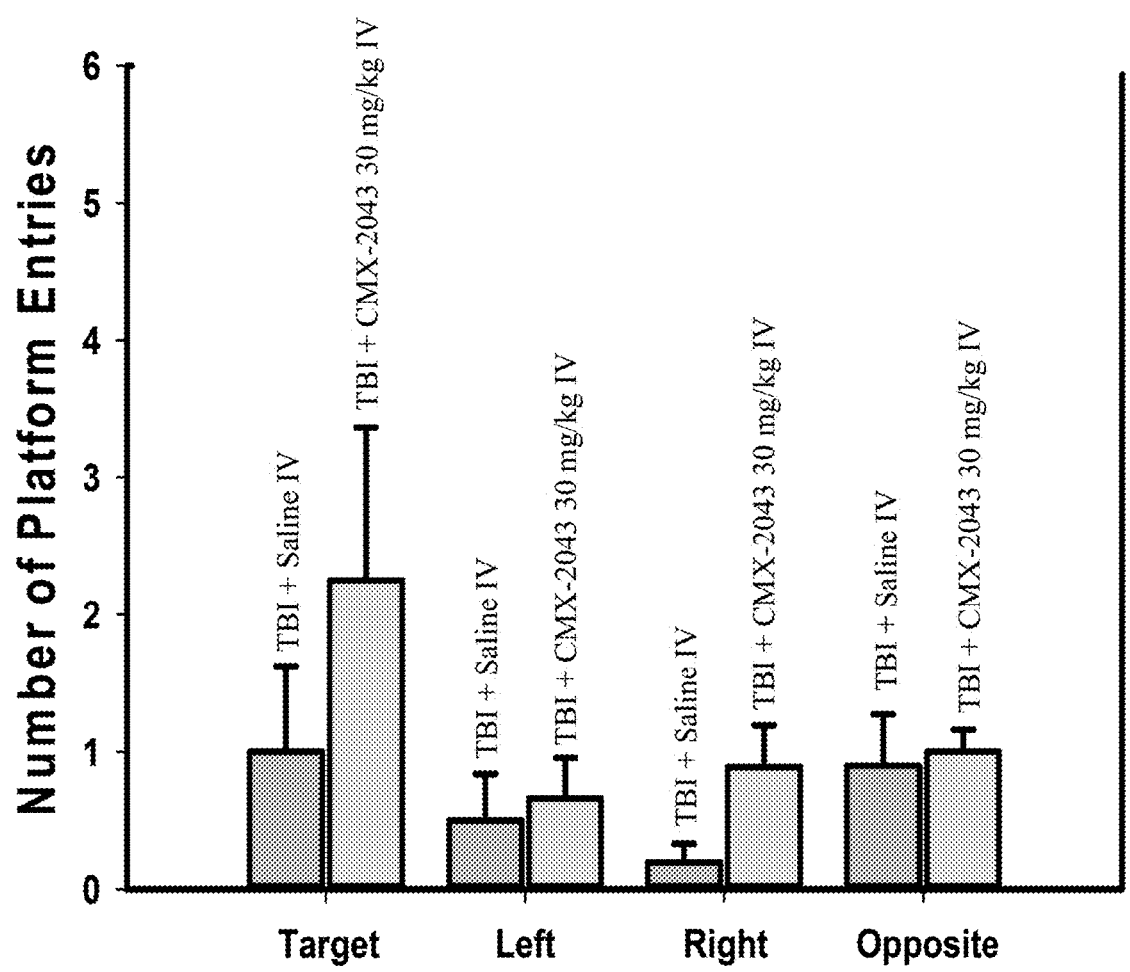
FIG. 12 shows the effect of TBI treatment with CMX-2043 on entries into target platform zones during Morris water maze probe trial. Data represent mean±SEM. n=10 Saline; n=9 CMX-2043.

Morris water maze probe trial: The effects of treatment with CMX-2043 on MWM probe trial performance in TBI-injured rats are shown in FIGS. 11 and 12.

On day 18 following surgery, animals underwent the Morris water maze probe trial, where they swam for 60 seconds in the water maze pool without the escape platform. The duration spent in the quadrant that previously contained the escape platform indicates learning of the platform location. The number of entries into the circular zone previously occupied by the platform is also measured.

ANOVA did not show an overall difference between treatment groups in the time spent in the target quadrant nor any differences in the other quadrants. ANOVA also did not reveal a significant difference in the number of entries into the platform zone previously occupied by the hidden platform.

Summary

This pre-clinical study showed significant efficacy in treating traumatic brain injuries with 30 mg/kg of CMX-2043 intravenously. Treatment efficacy was detected in the Morris water maze cognitive test but not in the beam balance motor test. This difference in efficacy may stem from differences in neuroprotection between regions of the injured brain. TBI results in both a primary lesion as well as a secondary cascade of neurodegenerative processes in regions distant from the injury epicenter. In the current study, the rat motor cortex is near the primary lesion epicenter in the medial frontal cortex. The results suggest that CMX-2043 may exert neuroprotection on regions distant from the lesion epicenter which are affected by the secondary degenerative processes initiated by TBI. One such region is the hippocampus, which is involved in the type of learning and memory that was observed to improve in the Morris water maze.

Example 3: CMX-2043 Improves Outcomes Following Focal Traumatic Brain Injury in a Porcine Model A study was designed to test whether CMX-2043 administration following focal traumatic brain injury would limit reductions in mitochondrial bioenergetics, mitochondrial reactive oxygen species generation (mtROS), and oxidative injury 24 hours post-TBI.

Study Design: A blinded, placebo controlled proof of concept trial of CMX-2043 was conducted in four-week-old piglets (8-10 kg). Piglets at this age have comparable neurodevelopment to a human toddler. Sixteen piglets (n=16) were designated into three cohorts: 1) Controlled cortical impact (CCI) at the rostral gyrus treated with a bolus of CMX-2043 (n=5), 2) CCI injured animals treated with placebo (n=5) and 3) sham animals (n=6). CMX-2043 treated animals received an intravenous loading bolus of CMX-2043 (13.4 mg/kg) 1 hour post-TBI and a 4.5 mg/kg bolus at 13 hours post-TBI. Subjects were intubated, ventilated and anesthesia maintained on isoflurane (1.0%). Buprenorphine (0.02 mg/kg IM) was administered for analgesia immediately following intubation. Monitors recorded oxygen saturation, heart rate, respiration rate, rectal temperature, and end tidal $CO_2$. Animals initially displayed confusion and ataxia devoid of apnea and returned to normal activity several hours later. All piglets were sacrificed between 24-25 hours post-TBI.

Mitochondrial Respiration and ROS Production: Twenty four hours post-CCI the ipsilateral penumbra and mirrored contralateral cortex were harvested. The rate of oxygen consumption was recorded via high-resolution Oroboros Oxygraph-2k™ with a specific Substrate-Uncouple-Inhibitor-Titration Protocol (SUIT). Complex I (OXPHOSCI) activity, was obtained after adding NADH-related substrates malate/pyruvate followed by ADP/glutamate. Next, succinate stimulated convergent electron input through the Q-junction (OXPHOSCI+CII). Then, oligomycin induced State 4 respiration (LEAKCI+CII) respiration independent of ATP production. Maximal reserve capacity of the electron transfer system (ETSCI+CII) was measured by titrating the protonophore carbonyl cyanide p-(trifluoro-methoxy) phenylhydrazone (FCCP). Finally, sequential additions of Complex I inhibitor rotenone, followed by ascorbate+tetramethylphenylenediamine (TMPD) and then sodium azide revealed Complex II (ETSCII) and Complex IV (CIV) respiration, serially. Mitochondrial reactive oxygen species production was measured in each respiratory phase by simultaneous quantitation of ROS-generation with an integrated fluorometer. High resolution respirometry evaluation with tissue homogenates minimizes cellular disruption, and closely mimics the physiologic environment crucial to mitochondrial networks and supercomplexes. Finally, to determine mitochondrial content of each sample a commercially available kit (Citrate Synthase Assay Kit, CS0720, Sigma) was used according to the manufacturer's instructions to determine citrate synthase (CS) activity.

Figure 13:
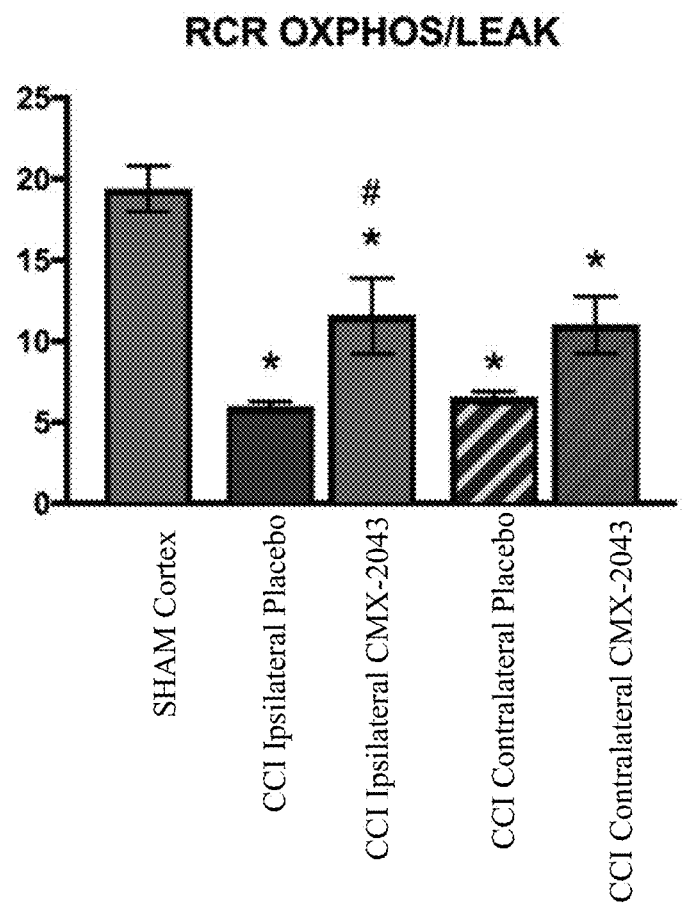
FIG. 13 shows the effect of CMX-2043 on respiratory control ratio (oxidative phosphorylation CI+CII/Leak respiration CI+CII) measured 24 hours post-CCI in a blinded placebo controlled proof of concept trial of CMX-2043 in a focal TBI model in piglets.

Mitochondrial Bioenergetics: Respiratory Control Ratio (Oxidative Phosphorylation CI+CII/Leak Respiration CI+CII) measured 24 hours post-CCI. FIG. 13 shows that the respiratory control ratio (RCR), a measure of overall mitochondrial health, was significantly decreased in both regions of CCI placebo treated animals (ipsilateral: 6.00.26, *$p<0.0001$; contralateral: 6.6±0.32, *$p<0.0001$) compared to sham cortex measurements (19.441.37). Piglets treated with an intravenous bolus of CMX-2043 one hour post-CCI and a repeat bolus 12 hours later displayed a treatment effect with a significantly increased ipsilateral RCR (CMX-2043 11.61±2.28, #$p<0.05$) compared to CCI ipsilateral placebo. The treated contralateral cortex did have an increase in RCR (11.05±1.71) but did not reach significance, P=0.09. Treatment with CMX-2043 did not maintain mitochondrial respiratory control ratios, measured in injured cortex, at sham levels in either region. Similar treatment effects were observed in the hippocampus.

Figure 14:
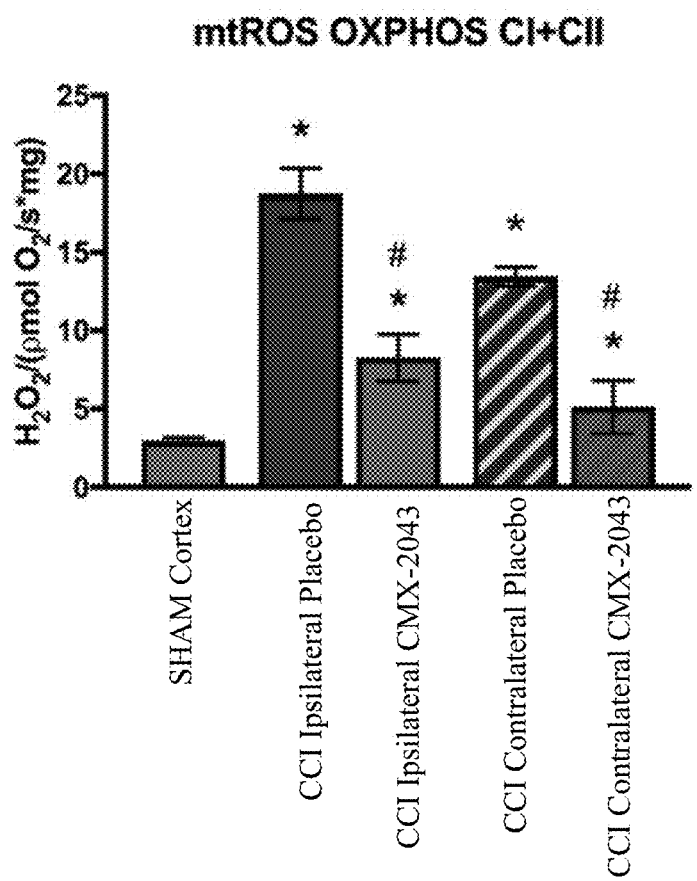
FIG. 14 shows the effect of CMX-2043 on mitochondrial reactive oxygen species generation measured 24 hours post-CCI in a blinded placebo controlled proof of concept trial of CMX-2043 in a focal TBI model in piglets.

Mitochondrial Reactive Oxygen Species: Blinded Placebo Controlled Proof of Concept Trial of CMX-2043: Mitochondrial Reactive Oxygen Species Generation Measured 24-Hours Post-CCI. Mitochondrial ROS (mtROS) generation was measured by simultaneous quantitation of ROS-generation with an integrated fluorometer during maximal oxidative phosyphorylation CI+CI respiration. FIG. 14 shows that mitochondrial ROS generation (in units of $H_2O_2/(\mu mol\ O_2 * mg)$) was significantly increased in both the ipsilateral and contralateral tissue in both injured cohorts with a *$p<0.001$. Specifically, mtROS generation in CCI ipsilateral treated with placebo was 18.77±1.58 units of $H_2O_2/(\mu mol\ O_2 * mg)$ ($p<0.0001$), CCI contralateral placebo was 13.7±0.58 units of $H_2O_2/(\mu mol\ O_2 * mg)$ ($p<0.0001$) and sham was 2.96±0.19 units of $H_2O_2/(\mu mol\ O_2 * mg)$. Animals treated with CMX-2043 post-TBI displayed a significantly lower mtROS production on both sides (ipsilateral: 8.28±1.47, $p<0.0001$; contralateral: 5.13±1.67, #$p<0.0001$) compared to respective regions from the CCI treated with placebo. Similar treatment effects were observed in the hippocampus.

Figure 15A:
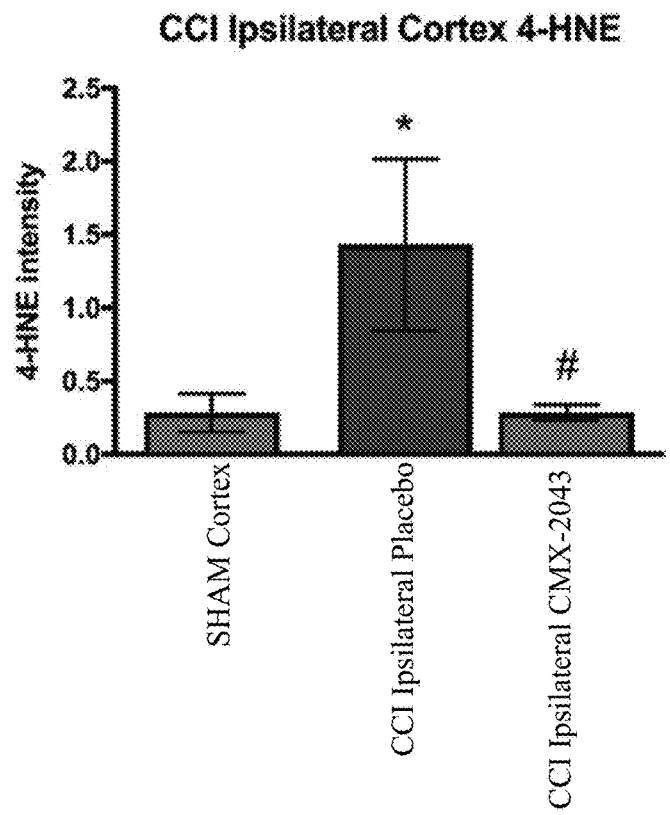
FIG. 15A shows lipid peroxidation measured by 4-hydroxynonenal (4-HNE) in cortical penumbra harvested from piglets post-CCI in a blinded placebo controlled proof of concept trial of CMX-2043 in a focal TBI model.

Oxidative Injury: FIG. 15A shows lipid peroxidation measured by 4-hydroxynonenal (4-HNE) measured in cortical penumbra. Samples from the same ipsilateral injured region analyzed for mtROS were analyzed for oxidative damage by measuring 4-HNE as an assessment of lipid peroxidation by Western Blot analysis (EMD Millipore), normalized by GAPDH (EMD Millipore), and compared to placebo and shams. Animals treated with CMX-2043 post-TBI displayed a significant reduction in lipid peroxidation compared to animals treated with placebo, #$p<0.001$. Similar therapeutic effects were observed in the hippocampus.

Figure 15B:
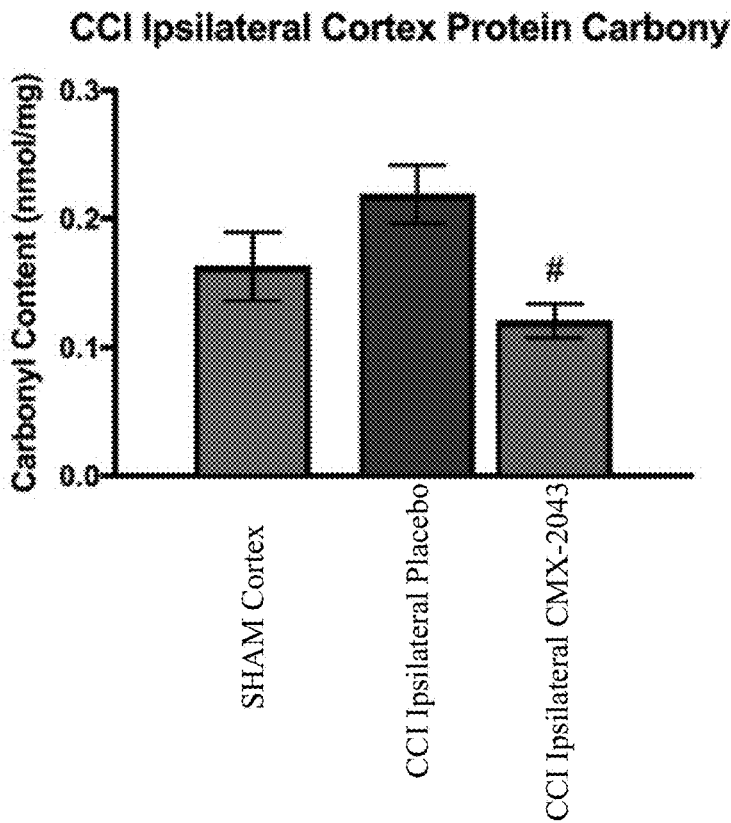
FIG. 15B shows protein carboxylation measured by ELISA in cortical penumbra harvested from piglets post-CCI in a blinded placebo controlled proof of concept trial of CMX-2043 in a focal TBI model.

FIG. 15B shows protein carboxylation measured by ELISA in cortical penumbra. Samples from the same ipsilateral region that were analyzed for mtROS were analyzed for oxidative damage by measuring protein carboxylation (VWR Int'l), and compared to placebo and shams. Animals treated with CMX-2043 post-TBI displayed a significant reduction in protein carboxylation compared to animals treated with placebo, #, $p<0.01$. Similar therapeutic effects were observed in the hippocampus.

These data show that CMX-2043 improves mitochondrial bioenergetics, and limits mitochondrial reactive oxygen species generation as well as oxidative injury following focal TBI.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the embodiments encompassed by the appended claims.

What is claimed is:

1. A method for treating traumatic brain injury in a subject in need thereof, comprising administering to the subject an effective amount of a compound of the following structural formula:

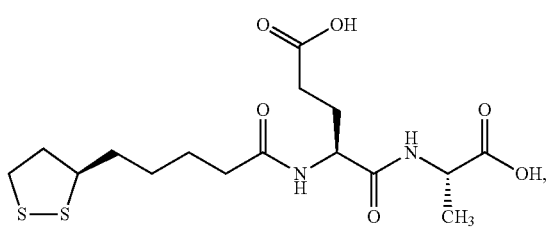 [SMILES: C[C@H](NC(=O)[C@H](CCC(=O)O)NC(=O)CCCC[C@@H]1CCSS1)C(=O)O]

or a pharmaceutically acceptable salt thereof.

2. The method of claim 1, comprising administering to the subject an effective amount of the compound.

3. The method of claim 1, comprising administering to the subject an effective amount of a pharmaceutically acceptable salt of the compound.

4. The method of claim 3, wherein the pharmaceutically acceptable salt comprises a monovalent cation or a divalent cation.

5. The method of claim 4, wherein the monovalent cation is a monovalent metal cation and the divalent cation is a divalent metal cation.

6. The method of claim 3, wherein the pharmaceutically acceptable salt comprises a sodium ion.

7. The method of claim 1, wherein the compound or pharmaceutically acceptable salt thereof is administered to the subject in a composition comprising a pharmaceutically acceptable carrier or diluent.

8. The method of claim 7, wherein the compound or pharmaceutically acceptable salt thereof is at least 90% enantiomerically pure in the composition.

9. The method of claim 1, wherein the compound or pharmaceutically acceptable salt thereof has a percent optical purity by weight of at least 99%.

10. The method of claim 1, wherein the subject is a human.

11. The method of claim 1, wherein the compound or pharmaceutically acceptable salt hereof is administered to the subject orally.

12. The method of claim 1, wherein the compound or pharmaceutically acceptable salt thereof is administered to the subject intravenously.

13. The method of claim 1, wherein the method is a method for treating neurodegenerative damage caused by traumatic brain injury.

14. The method of claim 13, wherein the neurodegenerative damage affects the hippocampus region of the brain.

15. The method of claim 14, wherein the neurodegenerative damage to the hippocampus region of the brain affects cognitive function associated with learning and memory.

16. The method of claim 13, wherein the neurodegenerative damage affects sensorimotor function.

17. The method of claim 13, wherein the neurodegenerative damage is associated with a focal or diffused traumatic brain injury.

18. The method of claim 13, wherein the neurodegenerative damage is secondary damage at a site other than the site of the primary lesion.

19. A method for inhibiting the generation of mitochondrial reactive oxygen species (mtROS) following a traumatic brain injury in a subject in need thereof, comprising administering to the subject an effective amount of a compound of the following structural formula:

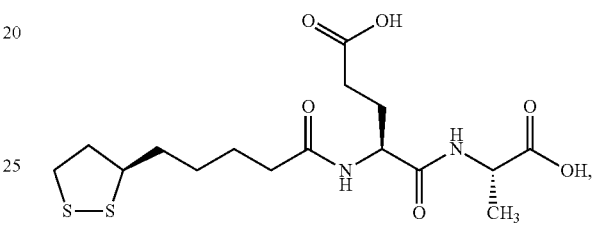

or a pharmaceutically acceptable salt thereof.

20. A method for improving mitochondrial bioenergetics following a traumatic brain injury in a subject in need thereof, comprising administering to the subject an effective amount of a compound of the following structural formula:

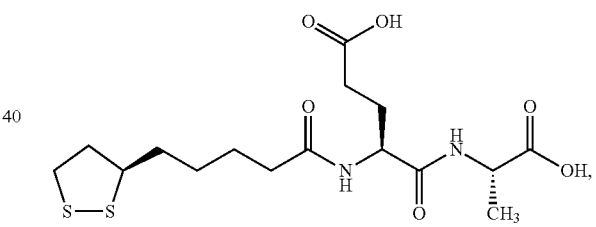

or a pharmaceutically acceptable salt thereof.

* * * * *